(12) United States Patent
Ignatyev et al.

(10) Patent No.: US 8,859,800 B2
(45) Date of Patent: Oct. 14, 2014

(54) COMPOUNDS CONTAINING ALKYL-ALKOXY-CYANO-BORATE ANIONS

(75) Inventors: Nikolai (Mykola) Ignatyev, Duisburg (DE); Michael Schulte, Bischofsheim (DE); Kentaro Kawata, Kanagawa (JP); Tomohisa Goto, Kanagawa (JP); Jan Sprenger, Rommerskirchen (DE); Maik Finze, Kleinrinderfeld (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/232,673

(22) PCT Filed: Jul. 6, 2012

(86) PCT No.: PCT/EP2012/002858
§ 371 (c)(1),
(2), (4) Date: Jan. 14, 2014

(87) PCT Pub. No.: WO2013/010640
PCT Pub. Date: Jan. 24, 2013

(65) Prior Publication Data
US 2014/0171656 A1 Jun. 19, 2014

(30) Foreign Application Priority Data
Jul. 15, 2011 (EP) ..................... 11005799

(51) Int. Cl.
*C07F 5/04* (2006.01)
*H01G 9/20* (2006.01)
(52) U.S. Cl.
CPC ............... *C07F 5/04* (2013.01); *H01G 9/2013* (2013.01)
USPC ...................................................... 558/384
(58) Field of Classification Search
USPC ........................................................ 558/384
See application file for complete search history.

(56) References Cited

U.S. PATENT DOCUMENTS

2002/0090547 A1* 7/2002 Schmidt et al. ............... 429/122

FOREIGN PATENT DOCUMENTS

WO 2005/021661 A1 3/2005

OTHER PUBLICATIONS

International Search Report dated Nov. 13, 2012 issued in corresponding PCT/EP2012/002858 application (pp. 1-3).
G. H. Torres et al., "Efficient Suzuki-Miyaura Coupling Reactions between Lithium Alkynyltrimethylborates and Aryl Chlorides", European Journal of Organic Chemistry, vol. 6 (2006) pp. 1450-1454.
D. Gabel et al., "Organometallics", Universitat Bremen, Science of Synthesis, vol. 6 (2004) pp. 541-561.
H. Yao et al., "Organo-Tricyanoborates as Tectons: Illustrative Coordination Polymers Based on Copper(I) Derivatives", Inorganic Chemistry, vol. 44, No. 18 (2005) pp. 6256-6264.
N. Koumura et al., "Alkyl-Functionalized Organic Dyes for Efficient Molecular Photovoltaics", J. Am. Chem. Soc., vol. 128 (2006) pp. 14256-14257.
R. Koster et al., "Organosubstituierte cis-1,2-Diborylalkene als Elektrophile Chelatbildner", Chem. Ber., vol. 126 (1993) pp. 305-317.
H. Witte et al., "Trialkylcyanoborate K[BR3CN]", Z. fur Naturforschung, vol. 22b (1967) pp. 1083.

* cited by examiner

*Primary Examiner* — Joseph Kosack
(74) *Attorney, Agent, or Firm* — Millen, White, Zelano & Branigan, P.C.

(57) ABSTRACT

The invention relates to new compounds containing alkyl-alkoxy-cyano-borate anions, their preparation and their use, in particular as part of electrolyte formulations for electrochemical or optoelectronic devices.

13 Claims, No Drawings

COMPOUNDS CONTAINING ALKYL-ALKOXY-CYANO-BORATE ANIONS

The invention relates to new compounds containing alkyl-alkoxy-cyano-borate anions, their preparation and their use, in particular as part of electrolyte formulations for electrochemical or optoelectronic devices.

The salts according to the invention can on the one hand be used for the synthesis of ionic liquids, on the other hand the salts can be employed per se as ionic liquid.

Ionic liquids or liquid salts are ionic species which consist of an organic cation and a generally inorganic anion. They do not contain any neutral molecules and usually have melting points below 373 K.

The area of ionic liquids is currently the subject of intensive research since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion.

E. Bernhardt et al, Z. Anorg. Allg. Chem. 2000, 626, 560, E. Bernhardt et al, Chem. Eur. J. 2001, 7, 4696 and E. Bernhardt et al, Z. Anorg. Allg. Chem. 2003, 629, 1229 disclose the novel chemically and electrochemically stable borate anions $[B(CN)_4]^-$, $[F_xB(CN)_{4-x}]^-$, where x=1 to 3, and $[B(CF_3)_4]^-$.

EP 1205480 A1 describes tetrakisfluoroalkylborate salts and the use thereof as conductive salts or ionic liquids.

The object of the present invention was to provide alternative compounds which are novel, thermally and electrochemically stable which can be used for the synthesis of ionic liquids or as ionic liquids or as conductive salts, and which are in particular useful for the synthesis of ionic liquids or as ionic liquids or organic salts for application in electrochemical or optoelectronic devices. The object of the present invention was furthermore to provide a method for the preparation of the alternative salts, especially the compounds of formula I, as described below, which can be produced in economical way on industrial scale.

The object is achieved by the salts of the formula I according to the invention with alkyl-alkoxy-cyano-borate anions and the described methods for their preparation.

The invention therefore relates to compounds of formula I

in which
$R^1$ denotes a straight-chain or branched alkyl group having 1 to 20 C atoms which optionally may contain at least one Cl, Br or I atom, at least one CN group and/or one or more oxygen or sulphur atoms, a straight-chain or branched alkenyl group having 2 to 20 C atoms and having one or more double bonds or a straight-chain or branched alkinyl group having 1 to 20 C atoms and having one or more triple bonds and optionally may have a double bond,
z is 1, 2, 3 or 4,
$R^*$ denotes a straight-chain or branched alkyl group having 1 to 20 C atoms and
$[Kt]^{z+}$ is an inorganic or organic cation.

The invention furthermore relates preferably to compounds of formula I, as described above, in which
$[Kt]^{z+}$ denotes
an inorganic cation selected from the group of $NO^+$, $H^+$, $Li^+$, $Na^+$, $K^+$, $Rb^+$, $Cs^+$, or $Mg^{2+}$, $Cu^+$, $Cu^{2+}$, $Zn^{2+}$, $Ag^+$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligands containing) metal cations which include rare-earths, transitions or noble metals like rhodium, ruthenium, iridium, palladium, platinum, osmium, cobalt, nickel, iron, chromium, molybdenum, tungsten, vanadium, titanium, zirconium, hafnium, thorium, uranium, gold,
or an organic cation selected from the group of
a tritylium cation, in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds,
an oxonium cation of formula (1) or a sulfonium cation of formula (2)

where $R°$ each independently of one another denotes a straight-chain or branched alkyl group having 1-8 C atoms, non-substituted phenyl or phenyl which is substituted by R', OR', $N(R')_2$, CN or halogen and in case of sulfonium cations of formula (2) additionally denotes each independently $(R''')_2N$— and R' is independently of each other H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and R''' is independently of each other straight-chain or branched $C_1$ to $C_6$ alkyl;
an ammonium cation, which conforms to the formula (3)

where
R in each case, independently of one another, denotes
H, OR', $N(R')_2$, with the proviso that a maximum of one R in formula (3) is OR' or $N(R')_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two R may be fully substituted by halogens, in particular —F and/or —Cl, and one or more of the substituents R may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, P(R')$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a phosphonium cation, which conforms to the formula (4)

[P(R²)₄]⁺ (4), where

R² in each case, independently of one another, denotes
H, OR' or N(R')₂,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two R² may be fully substituted by halogens, in particular —F and/or —Cl, and one or more of the substituents R² may be partially substituted by halogens, in particular —F and/or —Cl, and/or by —OH, —OR', —CN, —N(R')₂, —C(O)OH, —C(O)OR', —C(O)R', —C(O)N(R')₂, —SO₂N(R')₂, —C(O)X, —SO₂OH, —SO₂X, —NO₂, —SR', —S(O)R', —SO₂R' and where one or two non-adjacent carbon atoms in R² which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a uronium cation, which conforms to the formula (5)

[C(NR³R⁴)(OR⁵)(NR⁶R⁷)]⁺ (5), where

R³ to R⁷ each, independently of one another, denote
H, where H is excluded for R⁵,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents R³ to R⁷ may be fully substituted by halogens, in particular —F and/or —Cl, and one or more of the substituents R³ to R⁷ may be partially substituted by halogens, in particular —F and/or —Cl, and/or by –OH, —OR', —N(R')₂, —CN, —C(O)OH, —C(O)OR', —C(O)R', —C(O)N(R')₂, —SO₂N(R')₂, —C(O)X, —SO₂OH, —SO₂X, —SR', —S(O)R', —SO₂R', —NO₂ and where one or two non-adjacent carbon atoms in R³ to R⁷ which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, SO₂NR'—, —OP(O)R'O—, —P(O)(N(R')₂)NR'—, —P(R')₂=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a thiouronium cation, which conforms to the formula (6)

[C(NR³R⁴)(SR⁵)(NR⁶R⁷)]⁺ (6), where

R³ to R⁷ each, independently of one another, denote
H, where H is excluded for R⁵,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents R³ to R⁷ may be fully substituted by halogens, in particular —F and/or —Cl, and one or more of the substituents R³ to R⁷ may be partially substituted by halogens, in particular —F and/or —Cl, and/or by —OH, —OR', —N(R')₂, —CN, —C(O)OH, —C(O)OR', —C(O)R', —C(O)N(R')₂, —SO₂N(R')₂, —C(O)X, —SO₂OH, —SO₂X, —SR', —S(O)R', —SO₂R', —NO₂ and where one or two non-adjacent carbon atoms in R³ to R⁷ which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a guanidinium cation, which conforms to the formula (7)

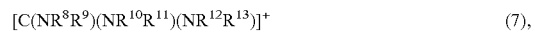

[C(NR⁸R⁹)(NR¹⁰R¹¹)(NR¹²R¹³)]⁺ (7), where

R⁸ to R¹³ each, independently of one another, denote
H, —CN, N(R')₂, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents R⁸ to R¹³ may be fully substituted by halogens, in particular —F and/or —Cl, and one or more of the substituents R⁸ to R¹³ may be partially substituted by halogens, in particular —F and/or —Cl, and/or by —OH, —OR', —N(R')₂, —CN, —C(O)OH, —C(O)OR', —C(O)R', —C(O)N(R')₂, —SO₂N(R')₂, —C(O)X, —SO₂OH, —SO₂X, —SR', —S(O)R', —SO₂R', —NO₂ and where one or two non-adjacent carbon atoms in R⁸ to R¹³ which are not in the α-position may be replaced by atoms and/or atom groups selected from the group —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a heterocyclic cation which conforms to the formula (8)

[HetN]^{z+} (8)

where

[HetN]$^{z+}$ denotes a heterocyclic cation selected from the group

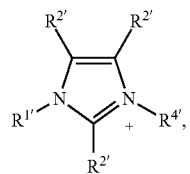
imidazolium

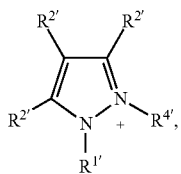
1H-pyrazolium

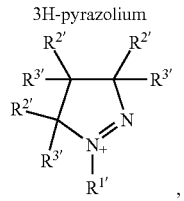
3H-pyrazolium

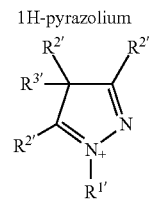
4H-pyrazolium

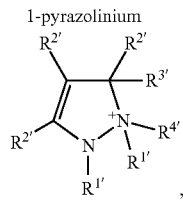
1-pyrazolinium

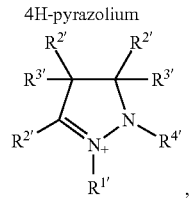
2-pyrazolinium

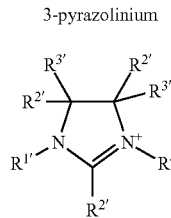
3-pyrazolinium

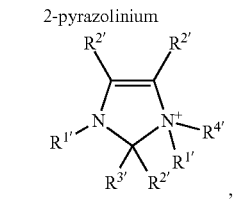
2,3-dihydroimidazolinium

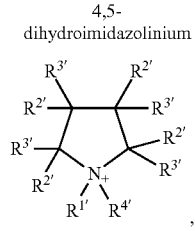
4,5-dihydroimidazolinium

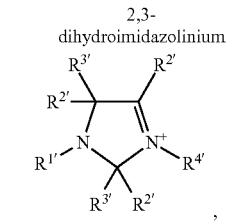
2,5-dihydroimidazolinium

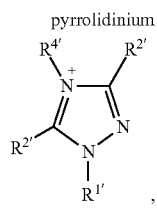
pyrrolidinium

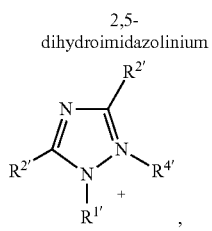
1,2,4-triazolium

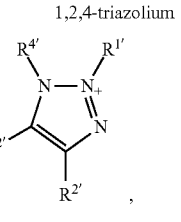
1,2,4-triazolium

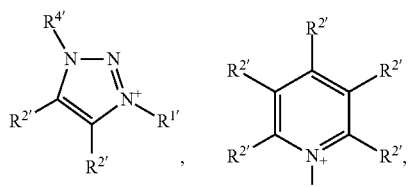
1,2,3-triazolium, pyridinium

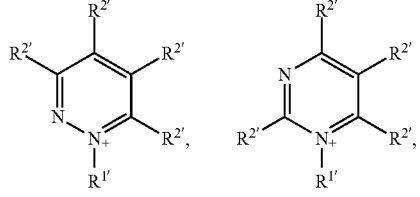
pyridazinium, pyrimidinium

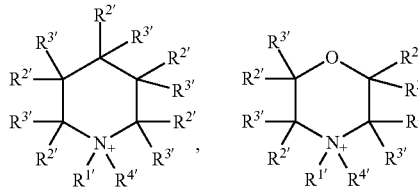
piperidinium, morpholinium

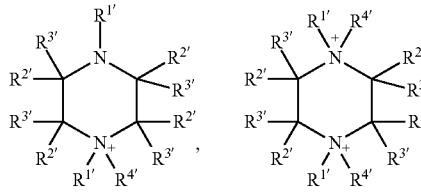
piperazinium, piperazinium

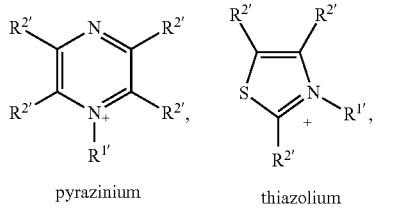
pyrazinium, thiazolium

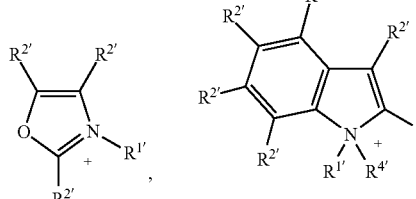
oxazolium, indolium

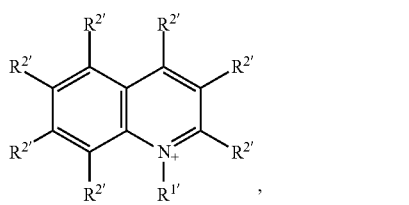
quinolinium

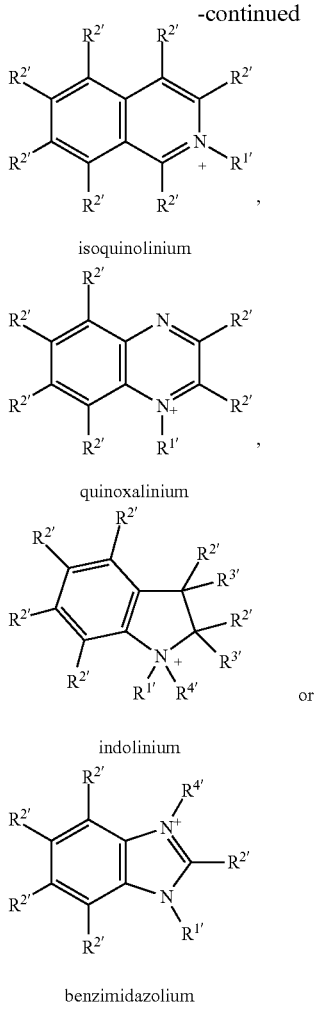

isoquinolinium quinoxalinium indolinium benzimidazolium where the substituents
$R^{1'}$ to $R^{4'}$ each, independently of one another, denote
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or alkyl groups having 1-6 C atoms,
saturated, partially or fully unsaturated heteroaryl, heteroaryl-$C_1$-$C_6$-alkyl or aryl-$C_1$-$C_6$-alkyl and $R^{2'}$ denote additionally F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that $R^{1'}$, $R^{3'}$, $R^{4'}$ are in this case independently of each other H and/or a straight-chain or branched alkyl having 1-20 C atoms, straight-chain or branched alkenyl having 2-20 C atoms and one or more double bonds,
where the substituents $R^{1'}$, $R^{2'}$, $R^{3'}$ and/or $R^{4'}$ together may also form a ring system,
where one to three substituents $R^{1'}$ to $R^{4'}$ may be fully substituted by halogens, in particular —F and/or —Cl, and one or more substituents $R^{1'}$ to $R^{4'}$ may be partially substituted by halogens, in particular —F and/or —Cl, and/or by —OH, —OR', N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$, but where $R^{1'}$ and $R^{4'}$ cannot simultaneously be fully substituted by halogens and where, in the substituents $R^{1'}$ to $R^{4'}$, one or two non-adjacent carbon atoms which are not bonded to the heteroatom may be replaced by atoms and/or atom groups selected from the —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen.

$R^1$ preferably denotes a straight-chain or branched alkyl group having 1 to 4 C atoms or a straight-chain or branched alkyl group having 1 to 4 C atoms in which one H atom is substituted by Br or CN or a straight-chain or branched alkyl group having 1 to 4 C atoms containing one oxygen atom. $R^1$ is particularly preferably methyl, ethyl, 1-bromomethyl, 1-cyanomethyl or methoxymethyl, very particularly preferably 1-cyanomethyl, 1-bromomethyl or methoxymethyl.

$R^*$ preferably denotes a straight-chain or branched alkyl group having 1 to 4 C atoms. $R^*$ particularly preferably denotes methyl, ethyl or n-butyl, very particularly preferably methyl or ethyl.

The compounds of formula I, as described or preferably described above or below having organic cations are possessing good thermal and electrochemical stabilities and are of interest for practical applications, for example in dye or quantum dot sensitized solar cells (DSSCs), Li- and Li-ion batteries and double-layer capacitors or in catalysis. Surprisingly, ionic liquids with alkyl-alkoxy-dicyanoborate anions having alkyl, alkoxy and cyano groups possess much lower viscosity in comparison to the viscosity of ionic liquids with tetrafluoroborate anion. This synergetic effect of alkyl, alkoxy and cyano groups on the properties (viscosity) of ionic liquids with alkyl-alkoxy-dicyanoborate anion is completely unexpected and is not predictable on the basis of existing knowledge.

Another advantage of compounds of formula I is that they can be prepared from commercially available starting materials via a simple reaction protocol.

Preferred inorganic cations $[Kt]^{z+}$ are metal cations, such as Li$^+$, Na$^+$, K$^+$, Rb$^+$, Cs$^+$, or Mg$^{2+}$, Cu$^+$, Cu$^{2+}$, Zn$^{2+}$, Ag$^+$, Ca$^{2+}$ and z is 1 or 2.

The alkali metal is preferably lithium which is preferably used as conducting salt and/or component of electrolytes for application in batteries, capacitors, sensors or for electrochemical processes, and sodium or potassium which is preferably used for the synthesis of compounds of formula I as described above and below in which the cation $[Kt]^{z+}$ is a cation other than the used sodium or the used potassium, especially preferably for compounds of formula I in which the cation $[Kt]^{z+}$ is an organic cation.

For organic cations, the following apply:
R° of the [(R°)$_3$O]$^+$ cation (formula (1)) or [(R°)$_3$S]$^+$ cation (formula (2)) is preferably straight-chain alkyl having 1-8 C atoms, preferably having 1-4 C atoms, in particular methyl or ethyl, very particularly preferably ethyl. A particularly preferred sulfonium cation is diethylmethylsulfonium.

For the purposes of the present invention, fully unsaturated cycloalkyl substituents are also taken to mean aromatic substituents.

In accordance with the invention, suitable substituents R and $R^2$ to $R^{13}$ of the compounds of the formulae (3) to (7) are preferably: H, $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl which may be substituted by $C_1$- to $C_6$-alkyl groups.

The substituents R and $R^2$ in the compounds of the formula (3) or (4) may be identical or different. The substituents R and $R^2$ are preferably different.

The substituents R and $R^2$ are particularly preferably methyl, ethyl, iso-propyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

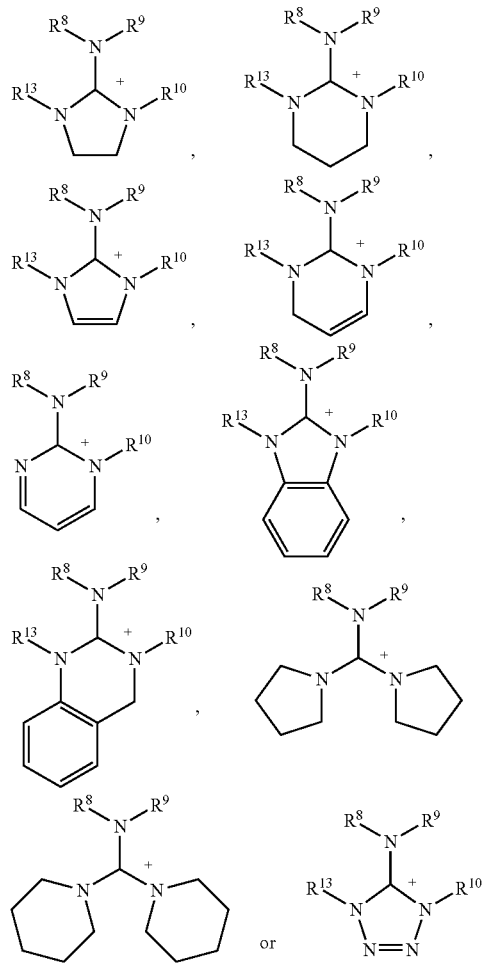

where the substituents $R^8$ to $R^{10}$ and $R^{13}$ can have a meaning or particularly preferred meaning indicated above.

If desired, the carbocycles or heterocycles of the guanidinium cations indicated above may also be substituted by straight-chain or branched $C_1$- to $C_6$-alkyl, straight-chain or branched $C_1$- to $C_6$-alkenyl, —CN, —$NO_2$, F, Cl, Br, I, OH, straight-chain or branched $C_1$-$C_6$-alkoxy, —N(R')$_2$, —SR', —S(O)R', —$SO_2$R', —COOH, —C(O)OR', —C(O)R', —C(O)N(R')$_2$, —$SO_2$N(R')$_2$, —C(O)X, —$SO_2$X, —$SO_3$H, substituted or non-substituted phenyl or a non-substituted or substituted heterocycle, where X and R' have a meaning indicated above.

Up to four substituents of the uronium cation $[C(NR^3R^4)(OR^5)(NR^6R^7)]^+$ or thiouronium cation $[C(NR^3R^4)(SR^5)(NR^6R^7)]^+$ may also be bonded in pairs in such a way that mono-, bi- or polycyclic cations are formed.

Without restricting generality, examples of such cations are indicated below, where Y=O or S:

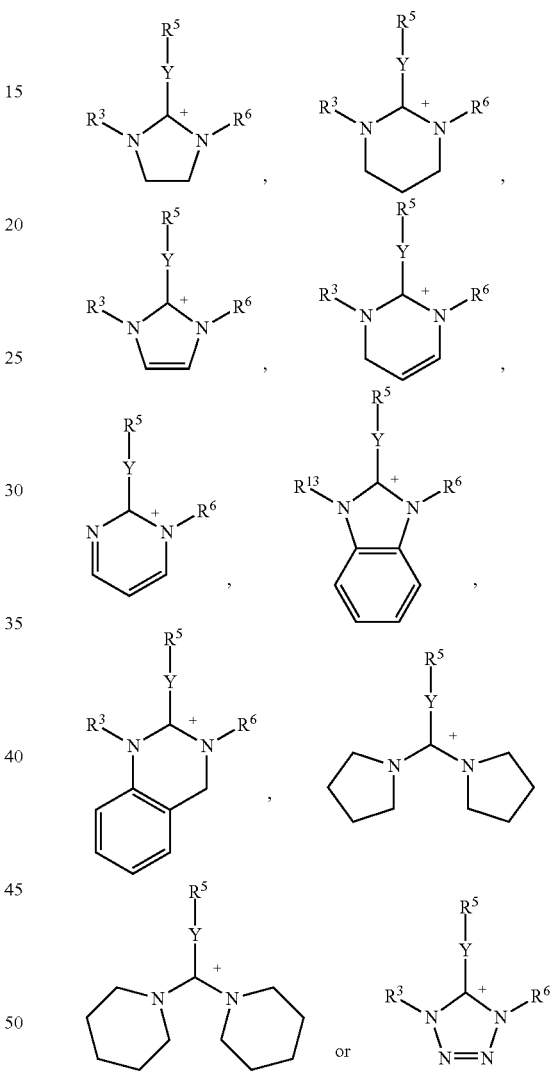

where the substituents $R^3$, $R^5$ and $R^6$ can have a meaning or particularly preferred meaning indicated above.

If desired, the carbocycles or heterocycles of the cations indicated above may also be substituted by straight-chain or branched $C_1$- to $C_6$-alkyl, straight-chain or branched $C_1$- to $C_6$-alkenyl, —CN, —$NO_2$, F, Cl, Br, I, OH, straight-chain or branched $C_1$-$C_6$-alkoxy, —N(R')$_2$, —SR', —S(O)R', —$SO_2$R', —COOH, —C(O)OR', —C(O)R', —C(O)N(R')$_2$, —$SO_2$N(R')$_2$, —C(O)X, —$SO_2$X, —$SO_3$H, substituted or non-substituted phenyl or a non-substituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formula (5) to (7) may be identical or different. $R^3$ to $R^{13}$ are particularly preferably each, independently of one another, methyl, ethyl, n-propyl, iso-propyl, n-butyl, tert-butyl, sec-butyl, phenyl, hexyl or cyclohexyl, very particularly preferably methyl, ethyl, n-propyl, iso-propyl, n-butyl or hexyl.

In accordance with the invention, suitable substituents $R^1$ to $R^{4'}$ of compounds of the formula (8) are each, independently of one another, preferably,

H, straight-chain or branched alkyl having 1 to 20 C atoms, which optionally may be fluorinated or perfluorinated, straight-chain or branched alkenyl having 2 to 20 C atoms and one or more double bonds, which optionally may be fluorinated, straight-chain or branched alkynyl having 2 to 20 C atoms and one or more triple bonds which optionally may be fluorinated or straight-chain or branched alkoxyalkyl having 2 to 8 C atoms, with the assumption that $R^{1'}$ and $R^{4'}$ are not simultaneously be perfluorinated.

The substituents $R^{1'}$ and $R^{4'}$ are each, independently of one another, particularly preferably straight-chain or branched alkyl having 1 to 20 C atoms, which optionally may be fluorinated or perfluorinated or straight-chain or branched alkoxyalkyl having 2 to 8 C atoms with the assumption that $R^{1'}$ and $R^{4'}$ are not perfluorinated at the same time.

The substituents $R^{1'}$ and $R^{4'}$ are each, independently of one another, particularly preferably methyl, ethyl, allyl, iso-propyl, propyl, butyl, sec-butyl, tert-butyl, n-pentyl, n-hexyl, n-octyl, n-decyl, cyclohexyl, methoxyethyl, methoxymethyl, ethoxyethyl or ethoxymethyl. They are very particularly preferably methyl, ethyl, propyl n-butyl or methoxyethyl. In pyrrolidinium, piperidinium or indolinium compounds, the two substituents $R^{1'}$ and $R^{4'}$ are preferably different.

In accordance with the invention, suitable substituents $R^{2'}$ and $R^{3'}$ of compounds of formula (8) are particularly preferably: H, straight-chain or branched $C_1$- to $C_{20}$-, in particular $C_1$- to $C_{12}$-alkyl groups.

The substituent $R^{2'}$ or $R^{3'}$ is in each case, independently of one another, in particular H, methyl, ethyl, iso-propyl, propyl, butyl, sec-butyl or tert-butyl. $R^{2'}$ is particularly preferably H, methyl, ethyl, iso-propyl, propyl, butyl or sec-butyl. $R^3$ is particularly preferably H. $R^{2'}$ and $R^{3'}$ are very particularly preferably H.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkenyl having 2 to 20 C atoms, in which a plurality of double bonds may also be present, is, for example, allyl, 2- or 3-butenyl, iso-butenyl, sec-butenyl, furthermore 4-pentenyl, iso-pentenyl, hexenyl, heptenyl, octenyl, —$C_9H_{17}$, —$C_{10}H_{19}$ to —$C_{20}H_{39}$, preferably allyl, 2- or 3-butenyl, iso-butenyl, sec-butenyl, furthermore preferably 4-pentenyl, iso-pentenyl or hexenyl, which may be optionally partially fluorinated.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl, which may be optionally partially fluorinated.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —N(R')$_2$, —CN, —C(O)OH, —C(O)N(R')$_2$, —SO$_2$N(R')$_2$, —C(O)X, —C(O)OR', —C(O)R', —SO$_2$OH, —SO$_2$X, —SR', —S(O)R', —SO$_2$R', —NO$_2$ and R' and X have a meaning as described above.

Non-substituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by straight-chain or branched $C_1$- to $C_6$-alkyl groups, where the cycloalkyl group or the cycloalkyl group substituted by straight-chain or branched $C_1$- to $C_6$-alkyl groups may in turn also be substituted by halogen atoms, such as F, Cl, Br or I, in particular F or Cl, or by —OH, —OR', —N(R')$_2$, —CN, —C(O)OH, —C(O)N(R')$_2$, —SO$_2$N(R')$_2$, —C(O)X, —C(O)OR', —C(O)R', —SO$_2$OH, —SO$_2$X, —SR', —S(O)R', —SO$_2$R', —NO$_2$ and R' and X have a meaning as described above.

In the substituents R, $R^2$ to $R^{13}$ or $R^{1'}$ to $R^{4'}$ one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R' is non-fluorinated, partially fluorinated or perfluorinated $C_1$- to $C_{18}$-alkyl, saturated $C_3$- to $C_7$-cycloalkyl, non-substituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_3$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', C$_3$- to C$_7$-cycloalkyl is, for example, cyclopropyl, cyclobutyl, cyclopentyl, cyclohexyl or cycloheptyl.

In R', substituted phenyl denotes phenyl which is substituted by straight-chain or branched C$_1$- to C$_6$-alkyl, straight-chain or branched C$_1$- to C$_6$-alkenyl, —CN, —NO$_2$, F, Cl, Br, I, —OH, straight-chain or branched-C$_1$-C$_6$-alkoxy, N(R'')$_2$, —COOH, —C(O)OR'', —C(O)R'', —SO$_2$X', —SR'', —S(O)R'', —SO$_2$R'', SO$_2$N(R'')$_2$ or SO$_3$H, where X' denotes F, Cl or Br and R' denotes a non-fluorinated, partially fluorinated or perfluorinated straight-chain or branched C$_1$- to C$_6$-alkyl or C$_3$- to C$_7$-cycloalkyl as defined for R', for example o-, m- or p-methylphenyl, o-, m- or p-ethylphenyl, o-, m- or p-propylphenyl, o-, m- or p-iso-propylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethyl-phenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R$^{1'}$ to R$^{4'}$, heteroaryl is taken to mean a saturated or unsaturated mono- or bicyclic heterocyclic group having 5 to 13 ring members, in which 1, 2 or 3 N and/or 1 or 2 S or O atoms may be present and the heterocyclic radical may be mono- or poly-substituted by straight-chain or branched C$_1$- to C$_6$-alkyl, straight-chain or branched C$_1$- to C$_6$-alkenyl, —CN, —NO$_2$, F, Cl, Br, I, —OH, —N(R'')$_2$, straight-chain or branched C$_1$-C$_6$-alkoxy, —COOH, —C(O)OR'', —C(O)R'', —SO$_2$X', —SO$_2$N(R'')$_2$, —SR'', —S(O)R'', —SO$_2$R'' or SO$_3$H, where X' and R'' have a meaning indicated above.

The heterocyclic group is preferably substituted or non-substituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-C$_1$-C$_6$-alkyl is, analogously to aryl-C$_1$-C$_6$-alkyl, taken to mean, for example, pyridinylmethyl, pyridinylethyl, pyridinylpropyl, pyridinylbutyl, pyridinylpentyl, pyridinylhexyl, where the heterocycles described above may furthermore be linked to the alkylene chain in this way.

HetN$^{z+}$ is preferably

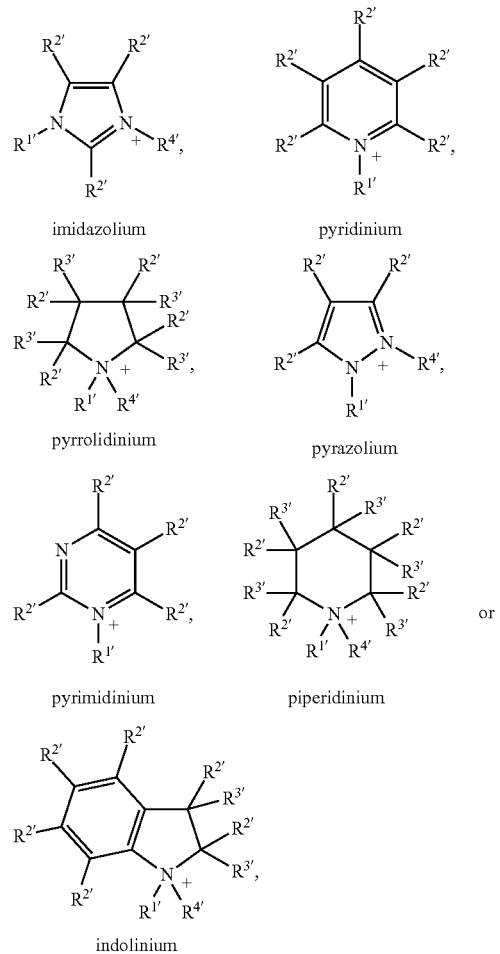

where the substituents R$^{1'}$ to R$^{4'}$ each, independently of one another, have a meaning described above.

HetN$^{z+}$ is particularly preferably

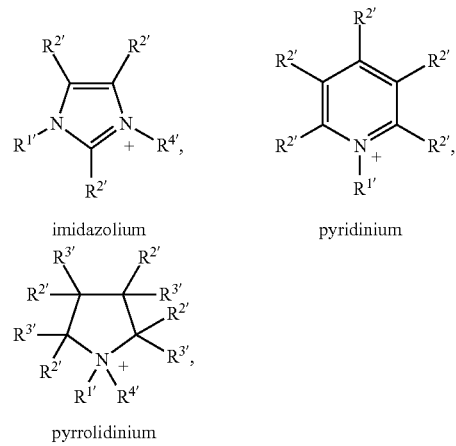

where the substituents R$^{1'}$ to R$^{4'}$ each, independently of one another, have a meaning described above.

HetN$^{z+}$ is very particularly preferably

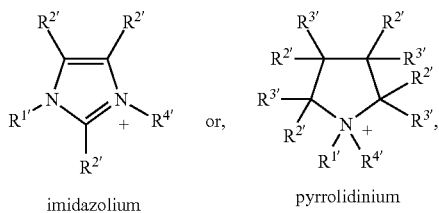

imidazolium      pyrrolidinium where the substituents R$^{1'}$ to R$^{4'}$ each, independently of one another, have a meaning described above. Preferred meanings of R$^{1'}$ to R$^{4'}$ within imidazolium or pyrrolidinium cations are defined in the following terms:

Preferred 1,1-dialkylpyrrolidinium cations are, for example, 1,1-dimethyl-pyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methyl-pyrrolidinium.

Preferred 1-alkyl-1-alkoxyalkylpyrrolidinium cations are, for example, 1-methoxymethyl-1-methyl-pyrrolidinium, 1-methoxymethyl-1-ethyl-pyrrolidinium, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium, 1-ethoxymethyl-1-ethyl-pyrrolidinium. Very particular preference is given to 1-(2-methoxyethyl)-1-methyl-pyrrolidinium.

Preferred 1,3-dialkylimidazolium cations are, for example, 1-ethyl-3-methyl-imidazolium, 1-methyl-3-propylimidazolium, 1,2,3-trimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methyl-imidazolium, 1-butyl-3-methylimidazolium or 1-methyl-3-propylimidazolium.

Preferred 1-alkoxyalkyl-3-alkylimidazolium cations are, for example 1-methoxymethyl-3-methylimidazolium, 1-methoxymethyl-3-ethylimidazolium, 1-methoxymethyl-3-butylimidazolium, 1-(2-methoxyethyl)-3-methyl-imidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methyl-imidazolium.

Preferred 1-alkenyl-3-alkylimidazolium cations are, for example 1-allyl-3-methyl-imidazolium or 1-allyl-2,3-dimethylimidazolium.

The organic cations of the compounds of formula I according to the invention are preferably sulfonium, ammonium, phosphonium cations of formulae (2), (3) and (4) or heterocyclic cations of formula (8), particularly preferably sulfonium cations of formula (2) or heterocyclic cations of formula (8) as described above.

The organic cations of the compounds of formula I according to the invention are very particularly preferably heterocyclic cations of formula (8) in which HetN$^{z+}$ is as defined above, where the substituents R$^{1'}$ to R$^{4'}$ each, independently of one another, have a meaning described or preferably described above. The organic cation of the compound of formula I is very particularly preferably imidazolium, where the substituents R$^{1'}$ to R$^{4'}$ each, independently of one another, have a meaning described above or has one of the particularly preferred meanings of 1,3-dialkylimidazolium, 1-alkenyl-3-alkylimidazolium or 1-alkoxyalkyl-3-alkylimidazolium as described above.

Particularly suitable organic cations of the formula I are 1-butyl-1-methyl-pyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributyl-methylammonium, tetra-n-butylammonium, tributyl-methylphosphonium, tetra-phenylphosphonium, diethyl-methylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-methyl-3-propinylimidazlium, 1,1-dimethylpyrrolidinium or trimethylsulfonium.

It goes without saying to the person skilled in the art that substituents, such as, for example, C, H, N, O, Cl, F, in the compounds according to the invention may be replaced by the corresponding isotopes.

Compounds of formula I in which [Kt]$^{z+}$ is Li$^+$ can be preferably used as conductive salts in primary batteries, secondary batteries, capacitors, supercapacitors or electrochemical cells, optionally also in combination with further conductive salts and/or additives, as constituent of a polymer electrolyte or phase-transfer medium.

Compounds of formula I, in which [Kt]$^{z+}$ is Na$^+$ or K$^+$ can be preferably used as starting materials for compounds of formula I in which [Kt]$^{z+}$ is an organic cation or another inorganic cation than sodium or potassium.

In addition, the invention relates to a process for the preparation of a compound of formula I as described or preferably described before comprising the reaction of a compound of formula II

[Kt]$^{z+}$[(R$^1$)BF$_3$]$^-$   II in which [Kt]$^{z+}$ and R$^1$ have a meaning as described or preferably described before with
a compound of formula III (Alkyl)$_3$SiOR*   III, in which the term "Alkyl" each independently denotes a straight-chain or branched alkyl group having 1 to 8 C atoms and R* has a meaning as described or preferably described above,
and trialkylsilylcyanide, in which the alkyl groups are each independently of one another straight-chain or branched alkyl having 1 to 8 C atoms.

Compounds of formula II in which [Kt]$^{z+}$ is an alkali metal cation are in most cases commercially available. Functionalized compounds of formula II in which [Kt]$^{z+}$ is an alkali metal cation can be prepared according to the procedure described in the literature [Molander, G. A. and B. Canturk. "Preparation of Potassium Alkoxymethyltrifluoroborates and Their Cross-Coupling with Aryl Chlorides." Organic Letters 10 (2008), pp. 2135-2138; Molander, G. A. and J. Ham "Synthesis of Functionalized Organotrifluoroborates via Halomethyltrifluoroborates." Organic Letters 8 (2006), pp. 2031-2034]. Other compounds of formula II can easily be synthesized by metathesis reaction as described below using the commercially available compounds of formula II as starting material.
Compounds of formula III (Alkyl)$_3$SiOR*   III, in which the term "Alkyl" each independently denotes a straight-chain or branched alkyl group having 1 to 8 C atoms and R* has a meaning as described or preferably described above are in most cases commercially available. The term "Alkyl" preferably denotes each independently a straight-chain or branched alkyl group having 1 to 4 C atoms, particularly preferably methyl, ethyl or n-butyl, very particularly preferably methyl or ethyl. Preferably, all three alkyl groups within the compound of formula III are equal.

Trialkylsilylcyanide in which the alkyl groups independently denotes straight-chain or branched alkyl groups having 1 to 8 C atoms are in some cases commercially available or can be synthesised by known processes.

For example, it is possible to generate trialkylsilylcyanide by the reaction of alkalimetalcyanide with trialkylsilylchloride in the presence of alkalimetaliodide and optionally elemental iodine (M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991; WO 2008/102661 A1).

The use of sodium cyanide and sodium iodide or potassium cyanide or potassium iodide is particular preferred. Preferably, the alkalimetaliodide will be used in 0.1 mol/l related to 1 mol/l alkalicyanide and trialkylsilylchloride. The reaction has to be carried out in a dry atmosphere, for example under dry air, nitrogen or argon.

The alkyl groups of trialkylsilylcyanide may be the same or different. Preferably, they are the same. Examples of trialkylsilylcyanides are such as trimethylsilylcyanide, triethylsilylcyanide, dimethylethylsilylcyanide, triisopropylsilylcyanide, tripropylsilylcyanide or tributylsilylcyanide. Particularly preferred is the use of trimethylsilylcyanide.

This process can be carried out in air, preferably in a dry atmosphere, for example under dry air, nitrogen or argon.

Trialkylsilylchloride can be used as additive in the above described process in excess of 0.1 mol % to 50 mol % to the other described reagents. Addition of catalytic quantities (0.1 mol % to 50 mol %) or excess of trialkylsilylchloride when trialkylsilylcyanide is generated in situ accelerate the reaction of the compound of formula II as described above with a compound of formula III and trialkylsilylcyanide. Without being bound by said theory it is believed that trialkylsilylchloride acts in this reaction as catalyst.

The reaction for the synthesis of compounds of formula I as described above carried out without a solvent or with a solvent using at least 2 equivalents of the trialkylsilylcyanide which is described above and at least one equivalent of the compound of formula III as described above. The reaction is preferably carried out in an organic solvent.

Preferred organic solvents are acetonitrile, propionitrile, benzonitrile, monoglyme, diglyme, tetrahydrofurane or dioxane, particularly preferably acetonitrile.

The reaction for the synthesis of compounds of formula I as described above is carried out at temperatures between 10° C. and 40° C., preferably at 20° C. to 25° C. which means at room temperature, and the reaction time is in the range of hours to days, preferably 12 to 24 hours. The reaction time can be reduced by addition of catalytic amount of trialkylsilylchloride.

Additionally, the invention is directed to a process for the preparation of a compound of formula I as described above, in which [Kt]$^{z+}$ is an organic cation,
comprising the reaction of a compound of formula II-1,

[Me]$^+$[(R$^1$)BF$_3$]$^-$   1 in which [Me]$^+$ denotes an alkali metal cation and R$^1$ has a meaning as described or preferably described above with
a compound of formula III (Alkyl)$_3$SiOR*   III, in which "Alkyl" each independently denotes a straight-chain or branched alkyl having 1 to 8 C atoms and R* has a meaning as described or preferably described above, and trialkylsilylcyanide, in which the alkyl groups are each independently of one another straight-chain or branched alkyl having 1 to 8 C atoms, in the presence or absence of trialkylsilylchloride as catalyst and further more with a compound of formula IV KtA   IV, in which
Kt has the meaning of the organic cation [Kt]$^{z+}$ and
A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [BF$_4$]$^-$, [PF$_6$]$^-$, [HSO$_4$]$^{1-}$, [NO$_3$]$^-$, [(R$_2$)$_2$P(O)O]$^-$, [R$_2$P(O)O$_2$]$^{2-}$, [(R$_1$O)$_2$P(O)O]$^-$, [(R$_1$O)P(O)O$_2$]$^{2-}$, [(R$_1$O)R$_1$P(O)O]$^-$, tosylate, malonate which may be substituted by straight-chain or branched alkyl groups having 1 to 4 C atoms or [HOCO]$_2{}^-$,
in which R$_1$ is each independently of another a straight-chain or branched alkyl group having 1 to 12 C atoms and
R$_2$ is each independently of one another a straight-chain or branched perfluorinated alkyl group having 1 to 12 C atoms and where electroneutrality should be taken into consideration in the formula of the salt KtA.

This reaction is carried out analogously to the process as described before but in a one pot procedure, the compound of formula KtA is added in at least one equivalent to the compound of formula II-1.

In addition, the invention relates to a process for the preparation of a compound of formula I in which $[Kt]^{z+}$ is an organic cation as described above or preferably described above, comprising the reaction of a compound of formula V $$[Kt]^{z+}[(R^1)BF_2(CN)]^- \qquad V$$

in which $[Kt]^{z+}$ and $R^1$ have a meaning as described or preferably described above with
a compound of formula III $$(Alkyl)_3SiOR^* \qquad III,$$

in which "Alkyl" each independently denotes a straight-chain or branched alkyl having 1 to 8 C atoms and R* has a meaning as described or preferably described above,
and trialkylsilylcyanide, in which the alkyl groups are each independently of one another straight-chain or branched alkyl having 1 to 8 C atoms.

The compounds of formula V in which $[Kt]^{z+}$ is an organic cation are not commercially available. Compounds of formula V in which $[Kt]^{z+}$ is an organic cation can be synthesized comprising the reaction of a compound of formula II $$[Kt]^{z+}[(R^1)BF_3]^- \qquad II$$

in which $[Kt]^{z+}$ denotes the organic cation and $R^1$ has a meaning as described above with trialkylsilylcyanide, in which the alkyl groups are each independently of one another straight-chain or branched alkyl having 1 to 8 C atoms in an organic solvent using 1 equivalent of the trialkylsilylcyanide which is described above. This reaction is carried out at room temperature within a reaction time of days, preferably 3 days.

A compound of formula V, prepared as described above, is reacted with at least 1 equivalent of trialkylsilylcyanide and at least 1 equivalent of a compound of formula III as described above. This reaction is carried out in an organic solvent as listed above, preferably acetonitrile and the reaction temperature is room temperature and the reaction time is hours, preferably 12 hours.

In addition, the invention relates to a process for the preparation of a compound of formula I according to claim 1, in which $[Kt]^{z+}$ is another cation than the used alkali metal cation in the starting material in a salt-exchange reaction, characterized in that an alkali metal salt of formula I-1

$$[Me]^+[(R^1)B(CN)_2(OR^*)]^- \qquad I-1$$

in which $[Me]^+$ is an alkali metal cation and $R^1$ and $R^*$ have a meaning as described above or preferably described above is reacted with a compound of formula IV $$KtA \qquad IV,$$

in which
Kt has a meaning of an organic cation or an inorganic cation other than the alkali metal cation of the compound of formula I-1 and
A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [SiF$_6$]$^{2-}$, [BF$_4$]$^-$, [PF$_6$]$^-$, [HSO$_4$]$^{1-}$, [NO$_3$]$^-$, [(R$_2$)$_2$P(O)O]$^-$, [R$_2$P(O)O$_2$]$^{2-}$, [(R$_1$O)$_2$P(O)O]$^-$, [(R$_1$O)P(O)O$_2$]$^{2-}$, [(R$_1$O)R$_1$P(O)O]$^-$, tosylate, malonate which may be substituted by straight-chain or branched alkyl groups having 1 to 4 C atoms, [HOCO$_2$]$^-$ or [CO$_3$]$^{2-}$ (merely for the synthesis of other compounds of formula I-1 having an other alkali metal cation than the starting material), in which $R_1$ is each independently of another a straight-chain or branched alkyl group having 1 to 12 C atoms and
$R_2$ is each independently of one another a straight-chain or branched perfluorinated alkyl group having 1 to 12 C atoms and where electroneutrality should be taken into consideration in the formula of the salt KtA.

$R_2$ is particularly preferably trifluoromethyl, pentafluoroethyl or nonafluorobutyl, very particularly preferably trifluoromethyl or pentafluoroethyl.

$R_1$ is particularly preferably methyl, ethyl, n-butyl, n-hexyl or n-octyl, very particularly preferably methyl or ethyl.

Compounds of formula I-1, as described above, are preferably used in the metathesis reaction as described above.

Substituted malonates are for example methyl malonate or ethyl malonate.

The compounds of formula IV are in most cases commercially available or can be synthesised by known processes. Known processes for the preparation of compounds of formula IV are described, for example, in P. Wasserscheid, T. Welton (Eds.), Ionic Liquids in Synthesis, Second Edition, WILEY-VCH, Weinheim, 2008.

The anion in the formula IV is preferably OH$^-$, Cl$^-$, Br$^-$, I$^-$, [HF$_2$]$^-$, [CN]$^-$, [SCN]$^-$, [CH$_3$OC(O)O]$^-$, [CH$_3$C(O)O]$^-$, [CH$_3$SO$_3$]$^-$, [CF$_3$C(O)O]$^-$, [CF$_3$SO$_3$]$^-$, [CH$_3$OSO$_3$]$^-$, [SiF$_6$]$^{2-}$, [BF$_4$]$^-$, [HSO$_4$]$^{1-}$, [NO$_3$]$^-$, [C$_2$H$_5$OSO$_3$]$^-$, [(C$_2$F$_5$)$_2$P(O)O]$^-$, [C$_2$F$_5$P(O)O$_2$]$^{2-}$, tosylates, malonates, [HCO$_3$]$^-$ and [CO$_3$]$^{2-}$ with the proviso that [CO$_3$]$^{2-}$ are used merely for the synthesis of compounds of formula I having another alkali metal cation than the alkali metal cation of the compound of formula I-1 or the anion in the formula IV is preferably OH, Cl$^-$, Br$^-$, I$^-$, [HF$_2$]$^-$, [SCN]$^-$, [CH$_3$C(O)O]$^-$, [CH$_3$C(O)O]$^-$, [CH$_3$SO$_3$]$^-$, [CF$_3$C(O)O]$^-$, [CF$_3$SO$_3$]$^-$, [CH$_3$OSO$_3$]$^-$, [SiF$^6$]$^{2-}$, [BF$_4$]$^-$, [PF$_6$]$^-$, [HSO$_4$]$^{1-}$, [NO$_3$]$^-$, [C$_2$H$_5$OSO$_3$]$^-$, [(C$_2$F$_5$)$_2$P(O)O]$^-$, [C$_2$F$_5$P(O)O$_2$]$^{2-}$, tosylates, malonates, [HCO$_3$]$^-$ and [CO$_3$]$^{2-}$ with the proviso that [CO$_3$]$^{2-}$ is used merely for the synthesis of compounds of formula I having another alkali metal cation than the alkali metal cation of the compound of formula I-1.

The anion in the formula IV is particularly preferably OH$^-$, Cl$^-$, Br$^-$, I$^-$, [CH$_3$SO$_3$]$^-$, [CH$_3$OSO$_3$]$^-$, [CF$_3$COO]$^-$, [CF$_3$SO$_3$]$^-$, [(C$_2$F$_5$)$_2$P(O)O]$^-$ or [CO$_3$]$^{2-}$ with the proviso that [CO$_3$]$^{2-}$ is used merely for the synthesis of compounds of formula I having another alkali metal cation than the alkali metal cation of the compound of formula I-1.

The anion in the formula IV is particularly preferably OH$^-$, Cl$^-$, Br$^-$, I$^-$, [CH$_3$SO$_3$]$^-$, [CH$_3$OSO$_3$]$^-$, [CF$_3$COO]$^-$, [CF$_3$SO$_3$]$^-$, [BF$_4$]$^-$, [PF$_6$]$^-$, [(C$_2$F$_5$)$_2$P(O)O]$^-$ or [CO$_3$]$_{[2]}^{2-}$ with the proviso that [CO$_3$]$^{2-}$ is used merely for the synthesis of compounds of formula I having another alkali metal cation than the alkali metal cation of the compound of formula I-1.

The anion in the formula IV is very particularly preferably OH$^-$, Cl$^-$, Br$^-$, [BF$_4$]$^-$, [PF$_6$]$^-$, [CH$_3$OSO$_3$]$^-$, [CF$_3$SO$_3$]$^-$, [CH$_3$SO$_3$]$^-$ for the synthesis of compounds of formula I having an inorganic cation and the anion in the formula IV is very particularly preferably OH$^-$, Cl$^-$, Br$^-$, [CH$_3$OSO$_3$]$^-$, [CF$_3$SO$_3$]$^-$, [CH$_3$SO$_3$]$^-$, [PF$_6$]$^-$ or [(C$_2$F$_5$)$_2$P(O)O]$^-$ for the synthesis of compounds of formula I having an organic cation.

Suitable organic salts for the preparation of the compounds of the formula I in which $[Kt]^{z+}$ is an organic cation are salts with cations of formula (1) to (8) or their preferred embodiments together with anions as defined as A described above or its preferred embodiments which means salts of cations of formula (1) to (8) or their preferred embodiments and OH$^-$, Cl$^-$, Br$^-$, [CH$_3$OSO$_3$]$^-$, [CF$_3$SO$_3$]$^-$, [CH$_3$SO$_3$]$^-$, [PF$_6$]$^-$ or [(C$_2$F$_5$)$_2$P(O)O]$^-$.

Suitable substances for the preparation of the compound of the formula I in which $[Kt]^{z+}$ is $H^+$ are aqueous $H[BF_4]$ and $H[PF_6]$ or $H[BF_4]$ and $H[PF_6]$ in organic solvents, preferably in diethylether or anhydrous HF, particularly preferably in diethylether. Reaction of $K[CH_3B(OCH_3)(CN)_2]$ or $Na[CH_3B(OCH_3)(CN)_2]$ with $H[BF_4]$ or $H[PF_6]$ results in the formation of $H[CH_3B(OCH_3)(CN)_2]$ in solvated form and poorly soluble potassium or sodium hexafluorophosphate or tetrafluoroborate.

Suitable inorganic salts for the preparation of the compounds of the formula I in which $[Kt]^{z+}$ is a metal cation e.g. from the group silver, magnesium, copper, zinc and calcium are, for example, $Ag_2O$, $Ag_2CO_3$, $MgCO_3$, $CuO$, $ZnO$, $Zn[HCO_3]_2$, $CaCO_3$ or $Ca(OC(O)CH_3)_2$. Useful salts for metathesis reaction to another alkali metal salt of formula I than potassium are e.g. $LiBF_4$ or $LiPF_6$.

The reaction is advantageously carried out in water in the case of the compounds of formula I-1 or in organic solvent, where temperatures of 10°-100° C., preferably 15°-60° C., particularly preferably room temperature, are suitable.

However, the reaction can alternatively also be carried out for the compounds of formula I in organic solvents at temperatures between 10° and 100° C. Suitable solvents here are acetonitrile, dialkylethers, tetrahydrofurane, dioxane, dichloromethane, dimethoxyethane or an alcohol, for example methanol, ethanol or iso-propanol.

The present invention furthermore relates to the use of the compounds of formula I as described above as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as entrainer, as extractant; as antistatic additive, as plasticiser; as heat-transfer-medium, as modifier for membranes and textile materials; as lubricant, as additive to lubricant compositions or to other engineering fluids; as hydraulic fluid or as additive to hydraulic fluids.

Preferably, compounds of formula I having inorganic cations as described above are useful as catalyst, as conducting salts, as components of electrolytes for the application in electrochemical cells, as components of supporting electrolytes for electrochemical processes, as surfactants, as phase-transfer catalysts or as antistatic additive.

Preferably, compounds of formula I having organic cations as described above or $H^+$ are useful as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as entrainer, as extractant; as antistatic additive, as plasticiser; as heat-transfer-medium, as modifier for membranes and textile materials; as lubricant, as additive to lubricant compositions or to other engineering fluids; as hydraulic fluid or as additive to hydraulic fluids.

In the case of the use of the said organic salts of formula I as media in catalytical processes or as solvents, these are suitable in any type of reaction known to the person skilled in the art, for example for transition-metal- or enzyme-catalysed reactions, such as, for example, hydroformylation reactions, oligomerisation reactions, esterifications or isomerisations, where the said list is not exhaustive.

On use as extractant, the organic salts of formula I can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials and as conductive salt or additive in various electrochemical cells and applications, for example in galvanic cells, in capacitors or in fuel cells.

Further fields of applications of the organic salts of formula I, according to this invention are solvents for carbohydrate containing solids in particular biopolymers and derivatives or degradation products thereof. In addition, these new compounds can be applied as lubricants, working fluids for machines, such as compressors, pumps or hydraulic devices. A further field of application is the field of particle or nanomaterial synthesis where these ionic liquids can act as medium or additive.

The compounds of formula I with organic cations, e.g. ionic liquids according to this invention may be preferably used in electrochemical and/or optoelectronic devices, especially in electrolyte formulations.

The present invention therefore relates furthermore to an electrolyte formulation comprising at least one compound of formula I as described above or preferably described.

Electrolyte formulations comprising compounds of formula I in which $[Kt]^{z+}$ is $Li^+$ or an organic cation can be preferably used in primary batteries, secondary batteries, capacitors, supercapacitors or electrochemical cells, optionally also in combination with further conductive salts and/or additives, as constituent of a polymer electrolyte or phase-transfer medium. Preferred batteries are lithium batteries or lithium-ion batteries. A preferred capacitor is a lithium-ion capacitor.

Electrolyte formulations comprising compounds of formula I can be preferably used in electrochemical and/or optoelectronic devices such as a photovoltaic cell, a light emitting device, an electrochromic or photo-electrochromic device, an electrochemical sensor and/or biosensor, particularly preferred in a dye-sensitized solar cell.

Such electrolyte formulations form a crucial part of the disclosed devices and the performance of the device largely depends on the physical and chemical properties of the various components of these electrolytes.

Factors which are still impeding the technical application of many electrochemical and/or optoelectronic devices and in particular of dye or quantum dot sensitized solar cells, are reliability problems caused by the volatility of organic solvents based electrolytes. It is very difficult to maintain a tight sealing of the electrolyte in e.g. a DSC panel, which has to withstand the temperature differences of daily day-night cycles and the concomitant thermal expansion of the electrolyte. The abbreviation DSC means dye sensitized solar cell. This problem can be solved in principle by the use of ionic liquid-based electrolytes. For review "Ionic liquid electrolytes for dye-sensitized solar cells" see: William R Pitner et al., "Application of Ionic Liquids in Electrolyte System" *Green Chemistry*. vol. 6, (2010). Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe so far the best power conversion efficiencies in ionic liquid-based electrolytes for DSC containing a significant quantity of organic salts with tetracyanoborate (TCB) anions.

Electrolyte formulations according to the invention are alternatives to already known electrolyte formulations. They show especially in the field of electrolyte formulations of dye sensitized solar cells a good performance particularly under high temperature. The advantage of the use of compounds of formula I having an organic cation and a alkyl-alkoxy-dicyanoborate anion is their low viscosity and thermal stability.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state and undergo dissociation into ionic species, i.e. supporting an electric conductivity via motion of ionic species. However, the said electric conductivity may not be of the major relevance to the role of the electrolyte of a dye-sensitized solar cell. Therefore, the scope of this invention is not limited to highly conductive electrolyte media.

The term electrolyte may be used for the term electrolyte formulation as well comprising all ingredients as disclosed for the electrolyte formulation.

Typical molar concentrations of the alkyl-alkoxy-dicyanoborate anion in the electrolyte formulations range from 0.1 to 5.5 M, preferably from 0.8 to 3.5 M. This molar concentration in the electrolyte may be achieved with one or more compounds of formula I in which $Kt^{z+}$ has a meaning as described or preferably described above.

Preferably, the molar concentration is achieved with at least one compound of formula I as described or preferably described above. For the purpose of the present invention, the molar concentration refer to the concentration at 25° C.

The present invention relates furthermore to an electrolyte formulation comprising at least one compound of formula I as described above or preferably described together with redox active species such as iodide/triiodide, Ferrocene derivatives or Co(II)/Co(III) complex couples such as Co(II)/Co(III)(dbbip)$_2$ in which dbbip means 2,6-bis(1-butylbenzimidazol-2-yl)pyridine, Co(II)/Co(III)(bpy)$_3$ where bpy denotes bipyridine or alkylated bipyridine derivates thereof, the counter anion being either perchlorate, fluoroperfluoroalkylphosphate such as perfluoroethylpentafluorophosphate, or (fluoro) cyanoborate, particularly tetracyanoborate, preferably a redox couple of iodine and at least one iodide salt.

The electrolyte formulation of the invention preferably comprises iodine (I$_2$). Preferably, it comprises from 0.0005 to 7 mol/dm$^3$, more preferably 0.01 to 5 mol/dm$^3$ and most preferably from 0.05 to 1 mol/dm$^3$ of I$_2$.

The iodide salt consists of an inorganic or organic cation and I$^-$ as anion. There exists no limitation to the kind of cation. However, to limit the amount of different cations in the electrolyte formulations, especially for DSC, organic cations shall be preferably used as already described for the compounds of formula I. Particularly preferably, the electrolyte formulation comprises at least one iodide salt in which the organic cation is independently selected from the group of

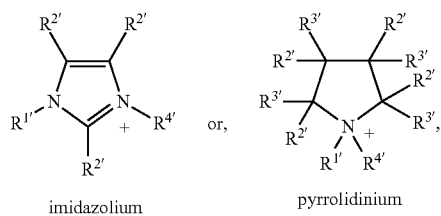

imidazolium    pyrrolidinium in which the substituents
R$^{2'}$ and R$^{3'}$ each, independently of one another, denote H or straight-chain or branched alkyl having 1 to 20 C atoms,
R$^{1'}$ and R$^{4'}$ each, independently of one another, denote straight-chain or branched alkyl having 1-20 C atoms, which optionally may be partially fluorinated or perfluorinated,
straight-chain or branched alkenyl having 2-20 C atoms and one or more double bonds, which optionally may be partially fluorinated,
straight-chain or branched alkynyl having 2-20 C atoms and one or more triple bonds, which optionally may be partially fluorinated.

Particularly preferred examples of the at least one iodide salt are 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) or N,N-dimethyl-pyrrolidinium iodide (mmpl I).

Other components of the electrolyte formulation are one or several further salts, solvents, and others, as indicated further below.

If the electrolyte formulation is a binary system, it comprises two salts, one further salt or iodide salt and a compound of formula I as described above. If the electrolyte formulation is a ternary system, it comprises two further salts and/or iodide salts and a compound of formula I as described above. The binary system comprises 90-10 weight %, preferably 70-30 weight %, more preferably 55-40 weight % of the further salt or iodide salt and 10-90 weight %, preferably 30-70 weight % or more preferably 45-60 weight % of the compound of formula I as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-10 weight. % in the electrolyte formulation according to the invention.

According to another embodiment of the present invention, the electrolyte formulation comprises at least one further salt with organic cations comprising a quaternary nitrogen and an anion selected from F, Cl, a polyhalide ion, a fluoroalkanesulfonate, a fluoroalkanecarboxylate, a tris(fluoroalkylsulfonyl)methide, a bis(fluoroalkylsulfonyl)imide, bis(fluorsulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane-chain having 1 to 20 C atoms, preferably perfluorinated, fluoroalkyl having 1 to 20 C atoms and alkyl having 1 to 20 C atoms. Fluoroalkane-chain or fluoroalkyl is preferably perfluorinated.

Preferably, the further salts are selected from salts comprising anions such as thiocyanate or tetracyanoborate, particularly preferred further salts are tetracyanoborates.

The cation of the at least one further salt or of a preferred further salt may be selected amongst organic cations as defined above for the compounds of formula I including also the preferred meanings.

In another embodiment of the invention, guanidinium thiocyanate may be added to the electrolyte formulation according to the invention.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention comprises less than 50 vol. % of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, butylene carbonate, gamma-butyrolactone, gamma-valerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate and methoxy-substituted nitriles. Other useful solvents are acetonitrile, benzonitrile and or valeronitrile.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic and/or electrochemical device such as a photovoltaic cell, a light emitting device, an electrochromic or photo-electrochromic device, an electrochemical sensor and/or biosensor.

The present invention therefore relates further to the use of the electrolyte formulation as described in detail above in an electrochemical and/or optoelectronic device which is a photovoltaic cell, a light emitting device, an electrochromic or photo-electrochromic device, an electrochemical sensor and/or or biosensor. Preferably, the electrolyte formulation may be used in dye sensitized solar cells.

The present invention therefore relates furthermore to an electrochemical and/or optoelectronic device which is a photovoltaic cell, a light emitting device, an electrochromic or photo-electrochromic device, an electrochemical sensor and/or or biosensor comprising an electrolyte formulation comprising at least one compound of formula I as described or preferably described above.

Preferably, the compound of formula I is a compound of formula I in which $[Kt]^{z+}$ is an organic cation as described above including all preferred meanings for application in dye-sensitized solar cells.

According to a preferred embodiment, the device of the present invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert it into electrical energy. There are no restrictions per se with respect to the choice of the dye as long as the LUMO energy state is marginally above the conduction bandedge of the photoelectrode to be sensitized. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20-7), D205 (CAS no. 936336-21-9), YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6) or terpyridine-Ruthenium dyes such as N749 (CAS no. 359415-47-7).

Particularly preferred dyes are Z907 or Z907Na which are both an amphiphilic ruthenium sensitizer or D205.

The structure of D205 is

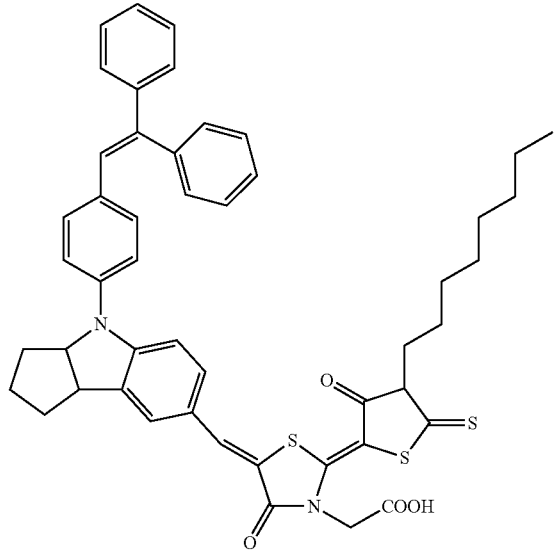

Very particularly preferred dyes are Z907 or Z907Na.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

The dye Z907Na means NaRu(2,2'-bipyridine-4-carboxylic acid-4'-carboxylate)(4,4'-dinonyl-2,2'-bipyridine)$(NCS)_2$.

For example, a dye-sensitized solar cell comprises a photoelectrode, a counter electrode and, between the photo-electrode and the counter electrode, an electrolyte formulation or a charge transporting material, and wherein a sensitizing dye is absorbed on the surface of the photo-electrode, on the side facing the counter electrode.

According to a preferred embodiment of the device according to the invention, it comprises a semiconductor, the electrolyte formulation as described above and a counter electrode.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semi-conducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be poured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The present invention will now be illustrated, without limiting its scope, by way of the following examples. Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

NMR samples were measured in 5 mm precision glass NMR tubes at 25° C. on a Bruker Avance III spectrometer equipped with a 9.3980 T cryomagnet. The $^1$H and $^{19}$F NMR spectra were acquired using a 5 mm combination $^1$H/$^{19}$F probe operating at 400.17 and 376.54 MHz, respectively. The $^{31}$P NMR spectra were obtained using a 5 mm broad-band inverse probe operating at 161.99 MHz. The $^1$H NMR chemical shifts were referenced with respect to tetramethylsilane (TMS) using the chemical shifts 2.05 ppm for the solvent Aceton-$D_6$. The $^{13}$C-NMR chemical shifts were referenced to the chemical shifts 29.9 ppm for the solvent Aceton-$D_6$. The $^{19}$F NMR spectra were referenced with respect to $CFCl_3$ using the internal standard $C_6H_5CF_3$ (−63.9 ppm). The $^{31}$P NMR spectra were referenced with respect to aqueous $H_3PO_4$ (85%).

The aceton-$D_6$ was used as a solvent and Deuterium lock if it is not given separately.

The disclosed viscosities are measured by means of Anton Paar Stabinger Viskosimeter SV 3000.

Example 1

1-Ethyl-3-methylimidazolium dicyanomethoxymethylborate—[EMIM][$CH_3B(OCH_3)(CN)_2$]

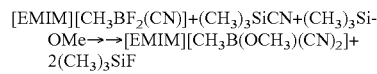

[EMIM][$CH_3BF_2(CN)$]+$(CH_3)_3SiCN$+$(CH_3)_3Si$-OMe→→[EMIM][$CH_3B(OCH_3)(CN)_2$]+2$(CH_3)_3SiF$

1-Ethyl-3-methylimidazolium cyanodifluoromethylborate, [EMIM]-[$CH_3BF_2(CN)$], 121 mg, 0.60 mmol), is dissolved in acetonitrile (2.5 ml), and methoxytrimethylsilane, $(CH_3)_3SiOCH_3$, (1.0 ml, 7.28 mmol) and trimethylsilyl cyanide (0.1 ml, 0.74 mmol) are added at room temperature. After 2 hours, all volatile constituents were removed in vacuo, giving an ionic liquid. The [EMIM][$CH_3B(OCH_3)(CN)_2$] comprises 3% of [EMIM]-[$CH_3BF(CN)_2$] and 2% of further impurities.

NMR data of the [$CH_3B(OCH_3)(CN)_2$]$^-$ anion:
$^{11}$B{$^1$H}-NMR: δ, ppm=−10.9 s.
$^{11}$B-NMR: δ, ppm=−10.8 s.
$^1$H{$^{11}$B}-NMR: δ, ppm=4.05 s ($CH_3$, 3H), 3.19 s ($CH_3O$, 3H), −0.19 s ($CH_3B$, 3H).
$^1$H-NMR: δ, ppm=3.19 br. s ($CH_3O$, 3H), −0.19 br. s ($CH_3B$, 3H).

NMR data of the [EMIM]$^+$ cation:
$^1$H-NMR: δ, ppm=9.28 s (CH, 1H), 7.79 t ($^3J_{H,H}$≈$^4J_{H,H}$≈1.7 Hz, CH, 1H), 7.72 t ($^3J_{H,H}$≈$^4J_{H,H}$≈1.7 Hz, CH, 1H), 4.40 q ($^3J_{H,H}$=7.3 Hz, $CH_2$, 2H), 4.05 s ($CH_3$, 3H), 1.56 t ($^3J_{H,H}$=7.3 Hz, $CH_3$, 3H).
Raman: ν (CN)=2187 cm$^{-1}$
MALDI-MS m/e [$C_4H_6BN_2O$]$^-$:
calculated: 109 (100%); 108 (25%); 110 (5%).
found: 109 (100%); 108 (23%); 110 (5%).

Example 2

Potassium bromomethylmethoxydicyanoborate, K[$BrCH_2B(OCH_3)(CN)_2$]

A)

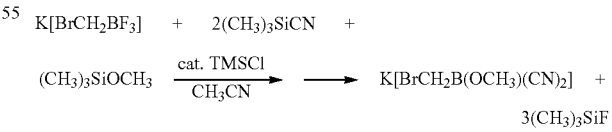

K[$BrCH_2BF_3$] + 2$(CH_3)_3SiCN$ + $(CH_3)_3SiOCH_3$ $\xrightarrow{\text{cat. TMSCl}}_{CH_3CN}$ K[$BrCH_2B(OCH_3)(CN)_2$] + 3$(CH_3)_3SiF$ K[$BrCH_2BF_3$](3.35 g, 16.68 mmol) is suspended in acetonitrile (90 mL) and trimethylsilylcyanide (11.12 mL, 83.40 mmol) and methoxytrimethylsilane (20.60 mL, 150.11 mmol) are added to the resulting suspension. Trimethylchlorosilane (0.50 mL, 3.96 mmol) is added to this mixture as a catalyst. The reaction mixture is stirred for 30 minutes at room temperature. All volatile compounds are removed under reduced pressure and used as starting materials for subsequent syntheses. The remaining light yellow solid is dissolved in acetone (15 mL) and by addition of $CHCl_3$ (150 mL) white $K[BrCH_2B(OCH_3)(CN)_2]$ is precipitated. The product is collected by filtration and dried in a vacuum.

The yield of potassium bromomethylmethoxydicyanoborate is 3.55 g (15.65 mmol),

The product, $K[BrCH_2B(OCH_3)(CN)_2]$, is characterised by means of NMR spectroscopy in $CD_3CN$.

$^{11}B$-NMR: δ, ppm=−10.7 (s).

$^1H\{^{11}B\}$-NMR: δ, ppm=3.22 (s, $OCH_3$, 3H), 2.44 (s, $CH_2Br$, 2H).

$^{13}C\{^1H\}$-NMR: δ, ppm=133.0 (q, $^1J_{C,B}$=61.8 Hz, CN, 2C), 53.3 (s, $OCH_3$, 1C), 29.0 (q, $^1J_{C,B}$=57.1 Hz, $CH_2Br$, 1C).

Raman spectrum of $K[BrCH_2B(OCH_3)(CN)_2]$: ṽ (CN)=2199 $cm^{-1}$.

B)

$K[BrCH_2BF_3]$ (0.50 g, 2.49 mmol) is reacted for 30 minutes with a mixture of trimethylsilylcyanide, methoxytrimethylsilane, and trimethylchlorosilane (25 mL) that was recycled from the previous synthesis (A) that approximately contained 10.74 mmol of $(CH_3)_3SiCN$, 28.98 mmol of $(CH_3)_3SiOCH_3$, and 0.86 mmol of $(CH_3)_3SiCl$. All volatiles are removed in vacuo and the resulting solid is dissolved in acetone (5 mL). Addition of $CHCl_3$ (50 mL) results in the precipitation of a white solid that is filtered off and dried in vacuo.

The yield of potassium bromomethylmethoxydicyanoborate is 0.49 g (2.16 mmol), The NMR spectra of the potassium bromomethylmethoxydicyanoborate obtained is identical to the spectra described in A).

C)

$K[BrCH_2BF_3]$ (2.60 g, 12.95 mmol) is reacted for 1.5 hours with a mixture of trimethylsilylcyanide, methoxytrimethylsilane, and trimethylchlorosilane (90 mL) that is recycled from the previous synthesis (B) that approximately contained 38.66 mmol of $(CH_3)_3SiCN$, 104.30 mmol of $(CH_3)_3SiOCH_3$, and 3.09 mmol of $(CH_3)_3SiCl$. All volatiles are removed in vacuo and the resulting solid is dissolved in acetone (15 mL). Addition of $CHCl_3$ (80 mL) results in the precipitation of a white solid that is filtered off and dried in vacuo.

The yield of potassium bromomethylmethoxydicyanoborate is 2.77 g (12.21 mmol), The NMR spectra of the potassium bromomethylmethoxydicyanoborate obtained are identical to the spectra described in A)

Example 3

1-Ethyl-3-methylimidazolium bromomethylmethoxydicyanoborate—[EMIM][BrCH_2B(OCH)(CN)_2]

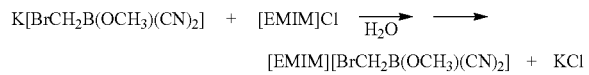

$K[BrCH_2B(OCH_3)(CN)_2]$ (6.63 g, 29.22 mmol) is suspended in $CH_2Cl_2$ (100 mL) and [EMIM]Cl (4.28 g, 29.22 mmol) is added. The suspension is vigorously stirred for 2 hours and subsequently filtered to remove the KCl that had formed. The KCl is washed with dichlormethane (50 mL). The combined organic phases are washed with aqua dest. (3×5 mL) and dried with $MgSO_4$ (15 g). The magnesium sulfate is removed via filtration. After removal of the solvent at 40° C. under reduced pressure the resulting ionic liquid is dried over night at 35° C. in vacuo.

The yield of 1-ethyl-3-methylimidazolium bromomethylmethoxydicyanoborate is 7.50 g (25.08 mmol).

$^{11}B$-NMR: δ, ppm=−10.7 (s).

$^1H\{^{11}B\}$-NMR: δ, ppm=9.06 (s, CH, 1H), 7.78 (s, CH, 1H), 7.71 (s, CH, 1H), 4.42 (q, $^3J_{H,H}$=7.3 Hz, $CH_2$, 2H), 4.08 (s, Me, 3H), 3.23 (s, $OCH_3$, 3H), 2.41 (s, $CH_2Br$, 2H), 1.58 (t, $^3J_{H,H}$=7.3 Hz, Me, 3H).

Example 4

Potassium bromomethylethoxydicyanoborat—$K[BrCH_2B(OEt)(CN)_2]$

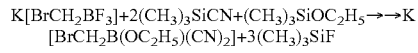

Potassium bromomethyltrifluoroborate, $K[BrCH_2BF_3]$ (100 mg, 0.498 mmol), is dissolved in a mixture of trimethylsilyl cyanide (3.0 ml, 22.49 mmol) and ethoxytrimethylsilane, $(CH_3)_3SiOC_2H_5$ (3.0 ml, 19.20 mmol), in acetonitrile (3.0 ml), and the mixture is stirred overnight at 50° C. and subsequently for 3 hours at 65° C. All volatile constituents are distilled off under reduced pressure and are used for further reactions. The residue obtained is dissolved in acetone (2 ml). Pale-brown potassium bromomethylethoxydicyanoborate is precipitated by addition of chloroform (20 ml), filtered off and dried in vacuo. The $K[BrCH_2B(OC_2H_5)(CN)_2]$ comprises 21% of $K[BrCH_2BF(CN)_2]$ and 2% of further unknown species. The product, $K[BrCH_2B(OC_2H_5)(CN)_2]$, can be purified by known methods.

NMR data of the $[BrCH_2B(OCH_2CH_3)(CN)_2]^-$ anion:

$^{11}B\{^1H\}$-NMR: δ, ppm=−11.3 s.

$^{11}B$-NMR: δ, ppm=−11.3 s.

$^1H\{^{11}B\}$-NMR: δ, ppm=3.48 q ($^3J_{H,H}$=7.0 Hz, $CH_2$, 2H), 2.40 s ($BrCH_2$, 2H), 1.07 t ($^3J_{H,H}$=7.0 Hz, $CH_3$, 3H).

$^1H$-NMR: δ, ppm=3.48 q ($^3J_{H,H}$=7.0 Hz, $CH_2$, 2H), 2.40 br. s ($BrCH_2$, 2H), 1.07 t ($^3J_{H,H}$=7.0 Hz, $CH_3$, 3H).

Raman spectrum: ṽ (CN)=2199 and 2217 $cm^{-1}$

MALDI-MS m/e $[C_5H_7BBrN_2O]^-$:
calculated: 201 (100%); 203 (98%); 202 (30%); 200 (25%); 204 (6%).
found: 201 (100%); 203 (98%); 202 (32%); 200 (24%); 204 (4%).

MALDI-MS m/e $[C_4H_2BBrFN_2O]^-$:
calculated: 175 (100%); 177 (98%); 176 (42%); 174 (25%); 178 (4%).
found: 175 (100%); 177 (96%); 176 (44%); 174 (29%); 178 (4%).

Example 5

Tetraphenylphosphoniumbromomethylethoxydicyanoborate—$[Ph_4P][BrCH_2B(OC_2H_5(CN)_2]$

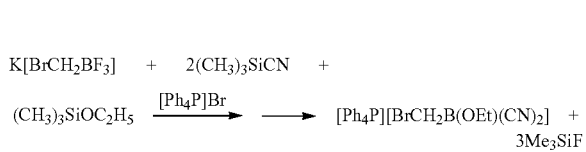

Potassium bromomethyltrifluoroborate, K[BrCH$_2$BF$_3$](20 mg, 0.099 mmol), is weighed out into an NMR tube with valve and a Teflon spindle (Young, London) and dissolved in a mixture of trimethylsilyl cyanide (0.3 ml, 2.249 mmol) and ethoxytrimethylsilane, (CH$_3$)$_3$SiOC$_2$H$_5$ (0.2 ml, 1.280 mmol), in acetonitrile (0.5 ml), and the mixture is warmed at 35° C. for 5 minutes. All volatile constituents are removed in vacuo. The residue is dissolved in deionised water, and the solution of [Ph$_4$P]Br (50 mg, 0.119 mmol) in deionised water (20 ml) is added. The precipitate formed is filtered off and dried in vacuo. The [Ph$_4$P][BrCH$_2$B(OC$_2$H$_5$)(CN)$_2$] comprises 29% of [Ph$_4$P][BrCH$_2$BF(CN)$_2$]. The product, [Ph$_4$P][BrCH$_2$B(OC$_2$H$_5$)(CN)$_2$], can be purified by known methods.

NMR data of the [BrCH$_2$B(OC$_2$H$_5$)(CN)$_2$]$^-$ anion:
$^{11}$B{$^1$H}-NMR: δ, ppm=−11.2 s.
$^{11}$B-NMR: δ, ppm=−11.2 s.
$^1$H{$^{11}$B}-NMR: δ, ppm=3.49 q ($^3J_{H,H}$=7.0 Hz, CH$_2$, 2H), 2.39 s (BrCH$_2$, 2H), 1.06 t ($^3J_{H,H}$=7.0 Hz, CH$_3$, 3H).
$^1$H-NMR: δ, ppm=3.49 q ($^3J_{H,H}$=7.0 Hz, CH$_2$, 2H), 2.39 br. s (BrCH$_2$, 2H), 1.06 t ($^3J_{H,H}$=7.0 Hz, CH$_3$, 3H).

NMR data of the [Ph$_4$P]$^+$ cation: $^1$H-NMR: δ, ppm=8.01 m (Ph, 4H), 7.87 m (Ph, 16H).

Example 6

1-Ethyl-3-methylimidazoliumdicyanomethoxymethylborate—[EMIM][CH$_3$B(OCH$_3$)(CN)$_2$]

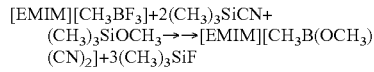

Trimethylsilyl cyanide (0.15 ml, 1.13 mmol) and methoxytrimethylsilane, (CH$_3$)$_3$SiOCH$_3$ (1.0 ml, 7.28 mmol), are added at 0° C. to a solution of 1-ethyl-3-methylimidazolium methyltrifluoroborate, [EMIM][CH$_3$BF$_3$](110 mg, 0.567 mmol), in acetonitrile (3 ml), and the mixture is stirred overnight at room temperature. Removal of the volatile constituents give an ionic liquid. The [EMIM][CH$_3$B(OCH$_3$)(CN)$_2$] comprises 14% of further species, inter alia 2% of [EMIM][CH$_3$BF(CN)$_2$].

The NMR data of [EMIM][CH$_3$B(OCH$_3$)(CN)$_2$] are analogous to those in Example 1.

Example 7

1-Ethyl-3-methylimidazoliumdicyanoethoxymethylborate—[EMIM][CHB(OC$_2$H$_5$)(CN)$_2$]

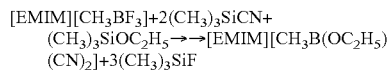

1-Ethyl-3-methylimidazolium methyltrifluoroborate, [EMIM][CH$_3$BF$_3$](110 mg, 0.567 mmol), is dissolved in acetonitrile (3 ml), and trimethylsilyl cyanide (0.15 ml, 1.13 mmol) is added. The reaction mixture is stirred for one hour, ethoxytrimethylsilane, (CH$_3$)$_3$SiOC$_2$H$_5$ (0.5 ml, 3.20 mmol), in acetonitrile (1 ml) is then added, and the mixture is stirred overnight. Removal of the volatile constituents give an ionic liquid.

The [EMIM][CH$_3$B(OC$_2$H$_5$)(CN)$_2$] comprises 25% of [EMIM][CH$_3$BF(CN)$_2$].

NMR data of the [CH$_3$B(OC$_2$H$_5$)(CN)$_2$]$^-$ anion:
$^{11}$B{$^1$H}-NMR: δ, ppm=−11.5 s.
$^{11}$B-NMR: δ, ppm=−11.5 s.
$^1$H{$^{11}$B}-NMR: δ, ppm=3.44 q ($^3J_{H,H}$=6.9 Hz, OCH$_2$, 2H), 1.04 t ($^3J_{H,H}$=7.0 Hz, CH$_3$, 3H), −0.18 s (CH$_3$B, 3H).
$^1$H{$^{11}$B}-NMR: δ, ppm=3.44 br. Q ($^3J_{H,H}$=6.9 Hz, OCH$_2$, 2H), 1.04 t ($^3J_{H,H}$=7.0 Hz, CH$_3$, 3H), −0.18 br. S (CH$_3$B, 3H).

NMR data of the [EMIM]$^+$ cation:
$^1$H-NMR: δ, ppm=9.83 s (CH, 1H), 7.90 t ($^3J_{H,H}$≈$^4J_{H,H}$=1.7 Hz, CH, 1H), 7.81 (t, $^3$JH,H≈$^4J_{H,H}$=1.7 Hz, CH, 1H), 4.43 (q, $^3J_{H,H}$=7.3 Hz, CH$_2$, 2H), 4.08 (s, Me, 3H), 1.56 (t, $^3J_{H,H}$=7.3 Hz, Me, 3H).

MALDI-MS m/e [C$_5$H$_8$BN$_2$O]$^-$:
calculated: 123 (100%); 122 (25%); 124 (7%).
found: 123 (100%); 122 (21%); 124 (3%).
MALDI-MS m/e [C$_3$H$_3$BFN$_2$]$^-$:
calculated: 97 (100%); 96 (25%); 98 (4%).
found: 97 (100%); 96 (22%); 98 (3%).

Example 8

Tetrabutylammoniumdicyanoethoxymethylborate—[TBA][CH$_3$B(OC$_2$H$_5$)(CN)$_2$]

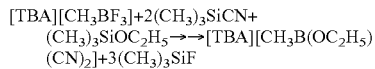

Tetrabutylammonium methyltrifluoroborate, [TBA][CH$_3$BF$_3$](250 mg, 0.768 mmol), is taken up in a solution of ethoxytrimethylsilane, (CH$_3$)$_3$SiOC$_2$H$_5$, in acetonitrile (2.1 M, 4.0 ml, 8.4 mmol), and the mixture is stirred for 12 hours. A solution of trimethylsilyl cyanide in acetonitrile (1.7 M, 0.9 ml, 1.53 mmol) is added to the suspension, and the mixture is stirred for 12 hours. Further ethoxytrimethylsilane dissolved in acetonitrile (2.1 M, 2.0 ml, 4.2 mmol) and trimethylsilyl cyanide (0.5 ml, 3.75 mmol) is subsequently added, and the mixture is stirred for one day. The reaction mixture is filtered, and all volatile constituents of the filtrate are removed in vacuo, giving a liquid residue. The product, tetrabutylammonium dicyanoethoxymethylborate, [TBA][CH$_3$B(OC$_2$H$_5$)(CN)$_2$], is characterised:
$^{11}$B{$^1$H}-NMR: δ, ppm=−11.5 s.
$^{11}$B-NMR: δ, ppm=−11.5 s.
$^1$H{$^{11}$B}-NMR: δ, ppm=3.48–3.44 m (CH$_2$, 8H), 3.45 q ($^3J_{H,H}$=6.9 Hz, OCH$_2$, 2H), 1.85–1.77 m (CH$_2$, 2H), 1.48–1.39 m (CH$_2$, 8H), 1.05 t ($^3J_{H,H}$=7.0 Hz, CH$_3$, 3H), 0.98 t ($^3J_{H,H}$=7.4 Hz, CH$_3$, 12H), —0.15 s (BCH$_3$, 3H).
$^1$H-NMR: δ, ppm=3.48-3.44 m (CH$_2$, 8H), 3.45 br. q ($^3J_{H,H}$=6.9 Hz, OCH$_2$, 2H), 1.85-1.77 m (CH$_2$, 8H), 1.48-1.39 m (CH$_2$, 8H), 1.05 t ($^3J_{H,H}$=7.0 Hz, CH$_3$, 3H), 0.98 t ($^3J_{H,H}$=7.4 Hz, CH$_3$, 12H), −0.15 br. s (BCH$_3$, 3H).
$^{13}$C{$^1$H}-NMR: δ, ppm=135.6 q ($^1J_{C,B}$=57 Hz, BCN, 2C), 61.0 s (OCH$_2$, 1 C), 59.4 s (4CH$_2$, 4C), 24.4 s (4CH$_2$, 4C), 20.4 s (4CH$_2$, 4C), 18.6 s (CH$_3$, 1C), 13.9 s (4CH$_3$, 4C), 8.8 q ($^1J_{C,B}$=52 Hz, BCH$_3$, 1C).
Raman-Spektrum: ṽ (CN)=2185 cm$^{-1}$.

Example 9

N-Butyl-N-methylpyrrolidiniumdicyanoethoxymethylborate—[BMPL][CH$_3$B(OC$_2$H$_5$)(CN)$_2$]

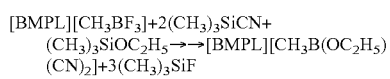

N-Butyl-N-methylpyrrolidinium methyltrifluoroborate, [BMPL][CH$_3$BF$_3$](250 mg, 1.11 mmol), is dissolved in a solution of ethoxytrimethylsilane, (CH$_3$)$_3$SiOC$_2$H$_5$, in acetonitrile (2.1 M, 4.0 ml, 8.4 mmol), and the mixture is stirred for 12 hours. A solution of trimethylsilyl cyanide in acetonitrile (1.7 M, 1.3 ml, 2.21 mmol) is added to the reaction mixture, which is then stirred for 12 hours. Further ethoxytrimethylsilane dissolved in acetonitrile (2.1 M, 2.0 ml, 4.2 mmol) and trimethylsilyl cyanide (0.5 ml, 3.75 mmol) is subsequently added, and the mixture is stirred for one day. All volatile constituents are removed in vacuo, giving a liquid residue.

The product, N-butyl-N-methylpyrrolidinium dicyanoethoxymethylborate, [BMPL][CH$_3$B(OC$_2$H$_5$)(CN)$_2$], is characterised:

$^{11}$B{$^1$H}-NMR: δ, ppm=−11.5 s.

$^{11}$B-NMR: δ, ppm=−11.5 s.

$^1$H{$^{11}$B}-NMR: δ, ppm=3.78-3.69 m (2CH$_2$, 4H), 3.61-3.56 m (CH$_2$, 2H), 3.43 q ($^3$J$_{H,H}$=7.0 Hz, OCH$_2$, 2H), 3.26 s (CH$_3$, 3H), 2.37-2.29 m (2CH$_2$, 4H), 1.92-1.84 m (CH$_2$, 2H), 1.48-1.39 m (CH$_2$, 2H), 1.05 t ($^3$J$_{H,H}$=7.0 Hz, CH$_3$, 3H), 0.98 t ($^3$J$_{H,H}$=7.4 Hz, CH$_3$, 3H), −0.16 s (BCH$_3$, 3H).

$^1$H-NMR: δ, ppm=3.78-3.69 m (2CH$_2$, 4H), 3.61-3.56 m (CH$_2$, 2H), 3.43 br. q ($^3$J$_{H,H}$=7.0 Hz, OCH$_2$, 2H), 3.26 s (CH$_3$, 3H), 2.37-2.29 m (2CH$_2$, 4H), 1.92-1.84 m (CH$_2$, 2H), 1.48-1.39 m (CH$_2$, 2H), 1.05 t ($^3$J$_{H,H}$=7.0 Hz, CH$_3$, 3H), 0.98 t ($^3$J$_{H,H}$=7.4 Hz, CH$_3$, 3H), −0.16 br. s (BCH$_3$, 3H).

$^{13}$C{$^1$H}-NMR: δ, ppm=136.1 q ($^1$J$_{C,B}$=57.3 Hz, BCN, 2C), 65.0 t ($^1$J$_{N,C}$=3.2 Hz, 2CH$_2$, 2C), 64.7 t ($^1$J$_{N,C}$=2.9 Hz, NCH$_2$, 1C), 60.9 s (OCH$_2$, 1C), 48.9 t ($^1$J$_{N,C}$=4.0 Hz, NCH$_3$, 1C), 26.3 s (CH$_2$, 1C), 22.3 s (CH$_2$, 1C), 20.4 t ($^2$J$_{N,C}$=1.4 Hz, 2CH$_2$, 2C), 18.5 (s, CH$_3$, 1C), 13.8 (s, CH$_3$, 1C), 8.7 q ($^1$J$_{C,B}$=51.4 Hz, BCH$_3$, 1 C).

Raman spectrum: $\tilde{\nu}$ (CN)=2185 cm$^{-1}$

Example 10

Potassium methoxymethyldicyanomethoxyborate—K[CH$_3$OCH$_2$B(OCH$_3$(CN)$_2$]

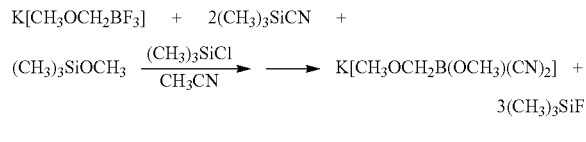

K[CH$_3$OCH$_2$BF$_3$](70 mg, 0.461 mmol) is suspended in 10 mL of a mixture of (CH$_3$)$_3$SiCN (4.29 mmol, 0.57 mL), (CH$_3$)$_3$SiOCH$_3$ (11.58 mmol, 1.59 mL), (CH$_3$)$_3$SiCl (0.79 mmol, 0.1 mL) and acetonitrile and stirred at room temperature for 30 minutes. Subsequently all volatile materials are removed in vacuo and a white solid is obtained.

The yield of potassium methoxymethyldicyanomethoxyborate is 80 mg (0.45 mmol).

The NMR spectra of K[CH$_3$OCH$_2$B(OCH$_3$)(CN)$_2$] are measured in CD$_3$CN.

$^{11}$B{$^1$H}-NMR; δ, ppm: −11.1 s.

$^{11}$B-NMR; δ, ppm: −11.1 s.

$^1$H{$^{11}$B}-NMR; δ, ppm: 3.23 s (CH$_2$OCH$_3$, 3H), 3.21 s (OCH$_3$, 3H), 2.75 s (CH$_2$, 2H).

$^1$H-NMR; δ, ppm: =3.23 s (CH$_2$OCH$_3$, 3H), 3.21 br. s (OCH$_3$, 3H), 2.75 br. s (CH$_2$, 2H).

The synthesis of 1-ethyl-3-methyl-imidazolium methoxymethyldicyanomethoxyborate and N-butyl-N-methyl-pyrrolidinium methoxymethyldicyanomethoxyborate is analogously to the Examples 3 and 9.

Example 11

Potassium cyanomethyldicyanomethoxyborate—K[CNCH$_2$B(OCH$_3$)(CN)$_2$]

A) KCN (6.15 mmol) and K[BrCH$_2$BF$_3$](0.819 mmol, commercially available) are suspended in acetonitrile (2 mL) and a solution of trimethylchlorsilane (0.3 mL, 2.38 mmol) in acetonitrile (5 mL) is added slowly. The suspension is stirred for 20 minutes at room temperature. The reaction mixture is filtered to remove all solid materials (excess of KCN as well as the side-product KCl). The solid material is washed with acetonitrile (2 mL) and the organic phases are combined. All volatile materials are removed under reduced pressure at 50° C. The obtained K[NCCH$_2$BF(CN)$_2$] is then reacted with methoxytrimethylsilane in acetonitrile according to Example 6 and the product K[NCCH$_2$B(OCH$_3$)(CN)$_2$] is obtained.

The synthesis of 1-ethyl-3-methyl-imidazolium cyanomethyldicyanomethoxyborate and N-butyl-N-methyl-pyrrolidinium cyanomethyldicyanomethoxyborate is analogously to the Examples 3 and 9.

B)

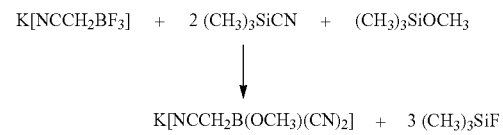

K[NCCH$_2$BF$_3$](6.8 g, 46.26 mmol) is dissolved in a mixture of recycled (CH$_3$)$_3$SiCN, (CH$_3$)$_3$SiCl, (CH$_3$)$_3$SiF, CH$_3$CN (100 mL, 86:4:7:3 mol %) and (CH$_3$)$_3$SiOCH$_3$ (30.0 mL, 218.4 mmol) and stirred at room temperature for 24 hours. The reaction mixture is filtered and the solid K[NCCH$_2$B(OCH$_3$)(CN)$_2$] is washed with CH$_2$Cl$_2$ (30 mL) and dried under reduced pressure.

The yield of K[NCCH$_2$B(OCH$_3$)(CN)$_2$] is 7.2 g (41.61 mmol which corresponds to 90% yield based on the starting material containing boron. The product contains 10% K[CH$_3$OB(CN)$_3$] and 3% K[NCCH$_2$BF(CN)$_2$].

$^{11}$B{$^1$H}-NMR: δ, ppm=−12.9 (s).

$^{11}$B-NMR: δ, ppm=−12.9 (s, broad).

$^1$H{$^{11}$B}-NMR: δ, ppm=3.21 (s, 3H, OCH$_3$), 1.28 (s, 2H, BCH$_2$).

$^1$H{$^{11}$B}-NMR: δ, ppm=3.21 (verbreitertes s, 3H, OCH$_3$), 1.28 (broad q, $^2$J$_{B,H}$≈5 Hz, 2H, BCH$_2$).

$^{13}$C{$^1$H}-NMR: δ, ppm=132.0 (q, $^1$J$_{C,B}$=65 Hz, BCN, 2C), 123.0 (s, CN, 1C), 53.3 (s, OCH$_3$, 1C), 10.5 (q, $^1$J$_{C,B}$=47 Hz, CH$_2$, 1C).

Elemental Analysis
calculated: C, 34.71; H, 2.91; N, 24.29.
found: C, 34.35; H, 2.68; N, 23.85.

C)

K[NCCH$_2$BF$_3$](100 mg, 0.68 mmol) is dissolved in a mixture (3 mL) of recycled trimethylsilylcyanide (86 mol %), fluorotrimethylsilane (4 mol %), chlorotrimethylsilane (3 mol %) and acetonitril (4 mol %). 1.0 mL (CH$_3$)$_3$SiOCH$_3$ (7.28 mmol) is added to the mixture and the suspension is stirred at room temperature for 12 hours. All volatile compounds are removed in vacuum and the solid K[NCCH$_2$B(OCH$_3$)(CN)$_2$] is identified. The yield is 116 mg (67 mmol) which corresponds to 99% based on the starting material containing boron.

The spectroscopic data of the product correspond to those of Example 11B.

Example 12

1-Ethyl-3-methylimidazolium Cyanomethyldicyanomethoxyborate—emim[NCCH$_2$B(OCH$_3$)(CN)$_2$]

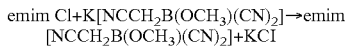

1-Ethyl-3-methylimidazolium chloride, (emimCl) (6.6 g, 45.40 mmol) and K[NCCH$_2$B(OCH$_3$)(CN)$_2$](7.1 g, 41.27 mmol) are dissolved in deionised water (50 mL) and the mixture is diluted with CH$_2$Cl$_2$ (70 mL). The aqueous phase is removed and the organic phase is washed with water (VE, 5×1 mL) and dried with magnesium sulfate. After filtration and distillation of methylene chloride, the ionic liquid is dried for three days at 50° C. in vacuum.

The product, 1-ethyl-3-methyl-imidazolium cyanomethyldicyanomethoxyborate, [emim][NCCH$_2$B(OCH$_3$)(CN)$_2$], is characterised:

Yield: 5.1 g (20.81 mmol, corresponding to 50% based on the starting borate. The liquid contains 10% emim[CH$_3$OB(CN)$_3$] and 2% emim[NCCH$_2$BF(CN)$_2$]$^-$).

$^{11}$B{$^1$H}-NMR: δ, ppm=−12.9 (s).
$^{11}$B-NMR: δ, ppm=−12.9 (s, broad).
$^{1}$H{$^{11}$B}-NMR: δ, ppm=8.92 (broad dd, $^4J_{H,H}$≈1.6 Hz, CH, 1H), 7.69 (dd, $^3J_{H,H}$≈1.8 Hz, CH, 1H), 7.63 (dd, $^3J_{H,H}$≈$^4J_{H,H}$≈1.8 Hz, CH, 1H), 4.36 (q, $^3J_{H,H}$=7.4 Hz, CH$_2$, 2H), 4.02 (s, CH$_3$, 3H), 3.21 (s, 3H, OCH$_3$), 1.55 (t, $^3J_{H,H}$=7.3 Hz, CH$_3$, 3H), 1.31 (s, 2H, BCH$_2$).
$^1$H-NMR: δ, ppm=8.92 (broad dd, $^4J_{H,H}$≈1.6 Hz, CH, 1H), 7.69 (dd, $^3J_{H,H}$≈$^4J_{H,H}$≈1.8 Hz, CH, 1H), 7.63 (dd, $^3J_{H,H}$≈H$^4J_{H,H}$≈1.8 Hz, CH, 1H), 4.36 (q, $^3J_{H,H}$=7.4 Hz, CH$_2$, 2H), 4.02 (s, CH$_3$, 3H), 3.21 (broad s, 3H, OCH$_3$), 1.55 (t, $^3J_{H,H}$=7.3 Hz, CH$_3$, 3H), 1.31 (broad q, $^2J_{B,H}$≈5 Hz, 2H, BCH$_2$).
$^{13}$C{$^1$H}-NMR: δ, ppm=136.6 (s, 1C), 132.1 (q, $^1J_{C,B}$=63.5 Hz, BCN, 2C), 124.5 (s, 1C), 123.1 (s, 1C), 122.8 (s, CN, 1C), 53.2 (s, OCH$_3$, 1C), 45.5 (s, 1C), 36.5 (s, 1C), 15.4 (s, 1C) 10.3 (q, $^1J_{C,B}$=46.3 Hz, CH$_2$, 1C).

Dynamic viscosity:

| ° C. | mPa · s |
|---|---|
| 20 | 50.1 |
| 40 | 21.0 |
| 60 | 11.1 |
| 80 | 6.8 |

Decomposition's temperature: 150° C.
Elemental Analysis:
calculated: C, 53.91; H, 6.58; N, 28.57.
found: C, 52.18; H, 6.65; N, 28.50.

Example A

Formulations and Device

The following electrolyte formulations are synthesized to demonstrate the application of electrolyte formulations according to the invention relative to electrolyte formulations of the prior art containing emim TCB in dye sensitized solar cells.

The electrolyte formulations are prepared through mixing of one or more of 1,3-dimethylimidazolium iodide (mmiml), 1-propyl-3-methyl-imidazolium iodide (pmiml), iodine, N-butylbenzimidazole (NBB) and guanidinium thiocyanate (guaSCN) and the corresponding ionic liquid as indicated such as emim TCB and emim methoxymethyldicyanomethoxyborate or bmpl TCB and bmpl methoxymethyldicyanomethoxyborate (N-butyl-N-methyl-pyrrolidinium methoxymethyldicyanomethoxyborate) in weight % as listed below.

| | weight % |
|---|---|
| Electrolyte 1 | |
| I$_2$ | 1.3 |
| mmim I | 35 |
| guaSCN | 0.7 |
| NBB | 3 |
| emim TCB | 60 |
| total | 100 |
| Electrolyte 2 | |
| I$_2$ | 1.3 |
| mmim I | 35 |
| guaSCN | 0.7 |
| NBB | 3 |
| emim [CH$_3$OCH$_2$B(CN)$_2$(OCH$_3$)] | 60 |
| total | 100 |
| Electrolyte 3 | |
| I$_2$ | 1.3 |
| mmim I | 35 |
| guaSCN | 0.7 |
| NBB | 3 |
| bmpl TCB | 60 |
| total | 100 |
| Electrolyte 4 | |
| I$_2$ | 1.3 |
| mmim I | 35 |
| guaSCN | 0.7 |
| NBB | 3 |
| bmpl [CH$_3$OCH$_2$B(CN)$_2$(OCH$_3$)] | 60 |
| total | 100 |

The above cited compounds are commercially available or are synthesized according to known literature methods or as described above.

The dye sensitized solar cells for the measurements (masterplates) are commercially available from ISE (Institut für solare Energiesysteme, Freiburg), serial no. 010311 which are fabricated based on the disclosure of U.S. Pat. No. 5,728,487 or WO 2007/093961:

The used titaniumdioxide paste is commercially available from Dyesol, Australia, serial no. DSL 18 NRT and DSL 18NRT AO.

The titanium dioxide is screen printed three times: two times with the titaniumdioxide paste DSL 18 NRT (each layer thickness=2 μm) and one time with the titaniumdioxide paste DSL 18NRT AO (layer thickness 5 to 6 μm).

The masterplate is irrigated with a solution of 30 mg Z907 dye in 62.5 ml ethanol for 6 hours.

The electrolyte formulations as described above are filled into the internal space of the prepared masterplate to produce the corresponding devices.

The dye Z907 is an amphiphilic ruthenium sensitizer Ru(2,2'-bipyridine 4,4'-dicarboxylic acid) (4,4'-dinonyl-2,2'-bipyridine)(NCS)$_2$ or synonymously [Ru(H2dcbpy)(dnbpy)(NCS)$_2$].

The measurements of photocurrent-voltage curves are carried out under Solarsimulator Sun 2000 from Abet Technologies, Model 11018, with temperature control for devices fabricated as described above containing electrolytes 1 to 6 placed on a black plate chilled down to 25° C. under 1 Sun illumination. The measured area of the solar cell is 5 mm to 25 mm.

Energy conversion efficiency is generally the ratio between the useful output of an energy conversion machine and the input of light radiation, in energy terms, determined by using adjustable resistant load to optimize the electric power output.

The following parameters characterize the measurements: $J_{sc}$=short circuit current [mAcm$^{-2}$], $V_{OC}$=open circuit voltage [V], FF=fill factor [%], η=power conversion efficiency [%].

The invention claimed is:
1. A compound of formula I

$$[Kt]^{z+}z[(R^1)B(CN)_2(OR^*)]^- \qquad I$$

in which
R$^1$ denotes a straight-chain or branched alkyl group having 1 to 20 C atoms which optionally contains at least one Cl, Br or I atom, at least one CN group and/or one or more oxygen or sulphur atoms, a straight-chain or branched alkenyl group having 2 to 20 C atoms and having one or more double bonds or a straight-chain or branched alkynyl group having 1 to 20 C atoms and having one or more triple bonds and optionally having a double bond,
z is 1, 2, 3 or 4,
R* denotes a straight-chain or branched alkyl group having 1 to 20 C atoms and [Kt]$^{z+}$ is an inorganic or organic cation.

2. A compound of formula I according to claim 1, wherein [Kt]$^{z+}$ denotes
NO$^+$, H$^+$, Li$^+$, Na$^+$, K$^+$, Rb$^+$, Cs$^+$, or Mg$^{2+}$, Cu$^+$, Cu$^{2+}$, Zn$^{2+}$, Ag$^+$, Ca$^{2+}$, Y$^{+3}$, Yb$^{+3}$, La$^{+3}$, Sc$^{+3}$, Ce$^{+3}$, Nd$^{+3}$, Tb$^{+3}$, Sm$^{+3}$, a complex ligand containing a metal cation, a rare-earth, a transition metal, a noble metal, rhodium, ruthenium, iridium, palladium, platinum, osmium, cobalt, nickel, iron, chromium, molybdenum, tungsten, vanadium, titanium, zirconium, hafnium, thorium, uranium, or gold, or
a tritylium cation, in which the phenyl groups is optionally substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds,
an oxonium cation of formula (1) or a sulfonium cation of formula (2)

$$[(R^o)_3O]^+ \qquad (1)$$

$$[(R^o)_3S]^+ \qquad (2),$$

where R$^o$ each independently of one another denotes a straight-chain or branched alkyl group having 1-8 C atoms, non-substituted phenyl or phenyl which is substituted by R', OR', N(R')$_2$, CN or halogen and in case of sulfonium cations of formula (2) additionally denotes each independently (R''')$_2$N—, and R' is independently of each other H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, and R''' is independently of each other straight-chain or branched C$_1$ to C$_6$ alkyl;
an ammonium cation of formula (3)

$$[NR_4]^+ \qquad (3),$$

where
R in each case, independently of one another, denotes
H, OR', N(R')$_2$, with the proviso that a maximum of one R in formula (3) is OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms,
where one or two R are optionally fully substituted by halogens, and one or more of the substituents R are optionally partially substituted by halogens, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', or —SO$_2$R', and where one or two non-adjacent carbon atoms in R which are not in the α-position are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;
a phosphonium cation of formula (4)

$$[P(R^2)_4]^+ \qquad (4),$$

where
R$^2$ in each case, independently of one another, denotes
H, OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms,
where one or two R$^2$ are optionally fully substituted by halogens, and one or more of the substituents R$^2$ are optionally partially substituted by halogens, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', or —SO$_2$R', and where one or two non-adjacent carbon atoms in R$^2$ which are not in the α-position are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched C$_1$- to C$_{18}$-alkyl, saturated C$_3$- to C$_7$-cycloalkyl, or non-substituted or substituted phenyl and X each independently is halogen;
a uronium cation of formula (5)

$$[C(NR^3R^4)(OR^5)(NR^6R^7)]^+ \qquad (5),$$

where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms, where one or two of the substituents $R^3$ to $R^7$ are optionally fully substituted by halogens, and one or more of the substituents $R^3$ to $R^7$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^3$ to $R^7$ which are not in the α-position are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, or non-substituted or substituted phenyl and X each independently is halogen;
a thiouronium cation of formula (6)

$$[C(NR^3R^4)(SR^5)(NR^6R^7)]^+ \quad (6),$$

where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms, where one or two of the substituents $R^3$ to $R^7$ are optionally fully substituted by halogens, and one or more of the substituents $R^3$ to $R^7$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^3$ to $R^7$ which are not in the α-position are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, or non-substituted or substituted phenyl and X each independently is halogen;
a guanidinium cation, which conforms to the formula (7)

$$[C(NR^8R^9)(NR^{10}R^{11})(NR^{12}R^{13})]^+ \quad (7),$$

where
$R^8$ to $R^{13}$ each, independently of one another, denote
H, —CN, N(R')$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or branched alkyl groups having 1-6 C atoms, where one or two of the substituents $R^8$ to $R^{13}$ are optionally fully substituted by halogens, and one or more of the substituents $R^8$ to $R^{13}$ are optionally partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^8$ to $R^{13}$ which are not in the α-position are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' each independently is H, non-fluorinated, partially fluorinated or perfluorinated straight-chain or branched $C_1$- to $C_{18}$-alkyl, saturated $C_3$- to $C_7$-cycloalkyl, or non-substituted or substituted phenyl and X each independently is halogen;
a heterocyclic cation of formula (8)

$$[HetN]^{z+} \quad (8)$$

where
HetN$^{z+}$ denotes one of the following cations

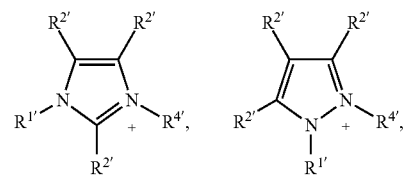

imidazolium      1H-pyrazolium

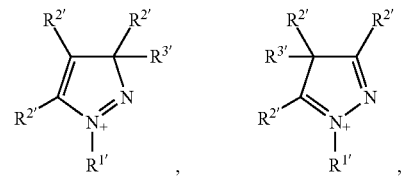

3H-pyrazolium      4H-pyrazolium

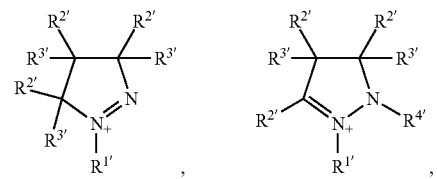

1-pyrazolinium      2-pyrazolinium

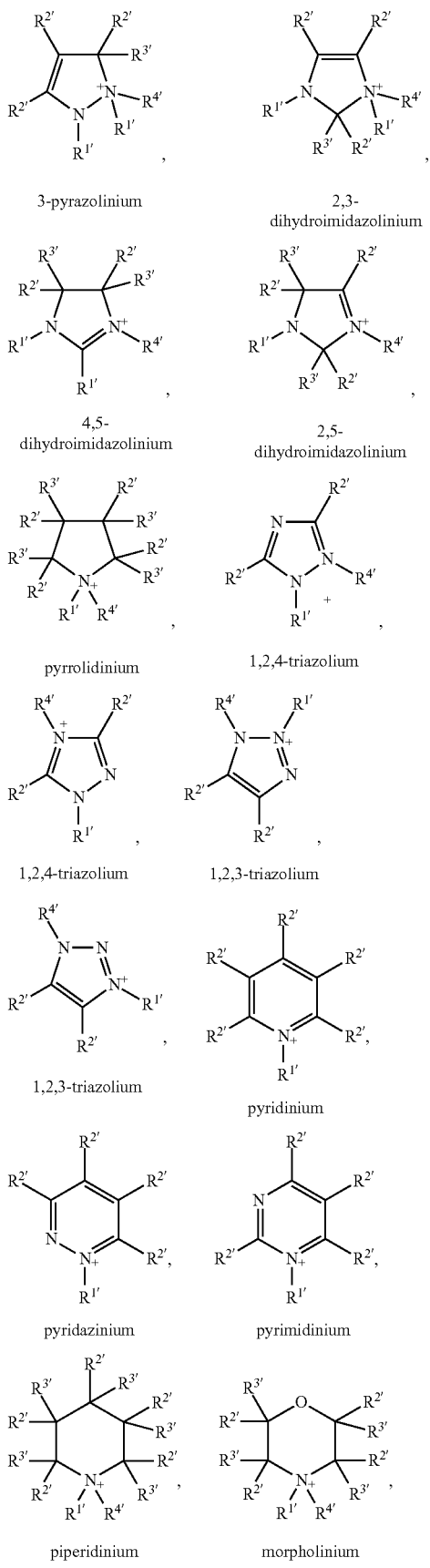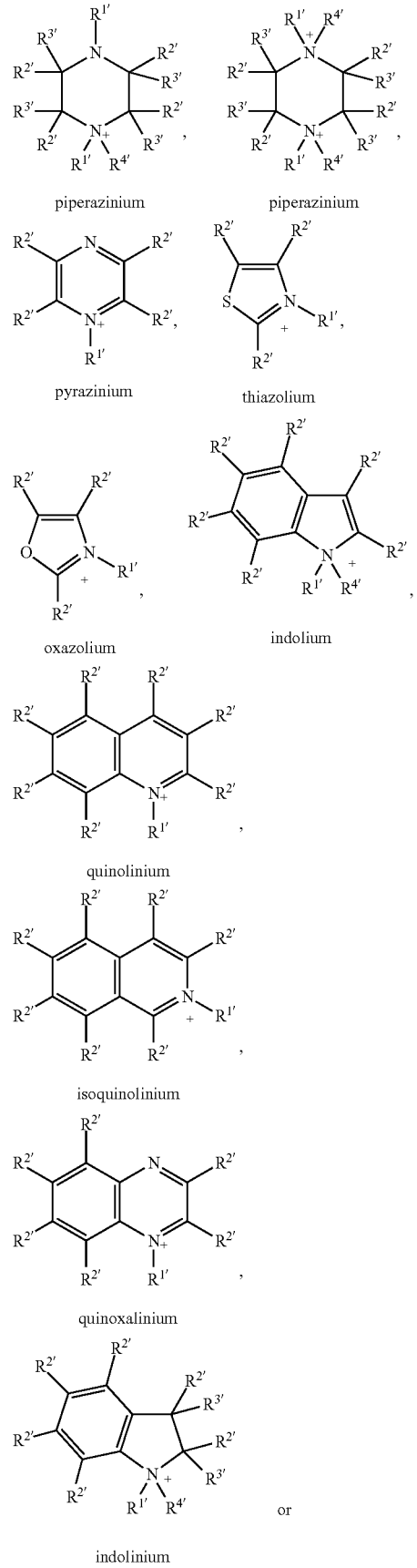

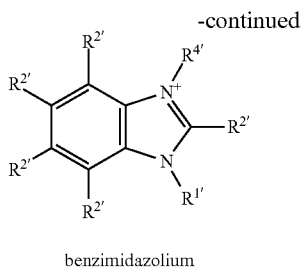

benzimidazolium where
$R^{1'}$ to $R^{4'}$ each, independently of one another, denote
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which is optionally substituted by straight-chain or alkyl groups having 1-6 C atoms, or
saturated, partially or fully unsaturated heteroaryl, heteroaryl-$C_1$-$C_6$-alkyl or aryl-$C_1$-$C_6$-alkyl and
$R^{2'}$ denote additionally F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that $R^{1'}$, $R^{3'}$, $R^{4'}$ are in this case independently of each other H and/or a straight-chain or branched alkyl having 1-20 C atoms, straight-chain or branched alkenyl having 2-20 C atoms and one or more double bonds,
or $R^{1'}$, $R^{2'}$, $R^{3'}$ and/or $R^{4'}$ together form a ring system, where one to three substituents $R^{1'}$ to $R^{4'}$ are optionally fully substituted by halogens, and one or more substituents $R^{1'}$ to $R^{4'}$ are optionally partially substituted by halogens, and/or by —OH, —OR', N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, but where $R^{1'}$ and $R^{4'}$ cannot simultaneously be fully substituted by halogens and where, in the substituents $R^{1'}$ to $R^{4'}$, one or two non-adjacent carbon atoms which are not bonded to the heteroatom are optionally replaced by atoms and/or atom groups —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
where R' each independently is H, non-fluorinated, partially fluorinated or perfluorinated straight-chain or branched $C_1$- to $C_{18}$-alkyl, saturated $C_3$- to $C_7$-cycloalkyl, or non-substituted or substituted phenyl and X each independently is halogen.

3. A compound of formula I according to claim 1, wherein $R^1$ in formula I is each independently a straight-chain or branched alkyl group having 1 to 4 C atoms or a straight-chain or branched alkyl group having 1 to 4 C atoms in which one H atom is substituted by Br or CN or a straight-chain or branched alkyl group having 1 to 4 C atoms containing one oxygen atom.

4. A process for preparing a compound of formula I according to claim 1, comprising reacting a compound of formula II $$[Kt]^{z+}[(R^1)BF_3]^-\qquad\qquad II$$

in which $[Kt]^{z+}$ and $R^1$ has a meaning as for the compound of formula I, with a compound of formula III $$(Alkyl)_3SiOR^*\qquad\qquad III,$$

in which "Alkyl" each independently denotes a straight-chain or branched alkyl having 1 to 8 C atoms and R* has a meaning as for the compound of formula I, or is trialkylsilylcyanide, in which the alkyl groups are each independently of one another straight-chain or branched alkyl having 1 to 8 C atoms.

5. A process for preparing a compound of formula I according to claim 1, in which $[Kt]^{z+}$ is an organic cation, comprising reacting a compound of formula II-1, $$[Me]^+[(R^1)BF_3]^-\qquad\qquad II-1$$

in which $[Me]^+$ denotes an alkali metal cation and $R^1$ has a meaning as for the compound of formula I,
with a compound of formula III $$(Alkyl)_3SiOR^*\qquad\qquad III,$$

in which "Alkyl" each independently denotes a straight-chain or branched alkyl having 1 to 8 C atoms and R* has a meaning as for the compound of formula I, or is trialkylsilylcyanide, in which the alkyl groups are each independently of one another straight-chain or branched alkyl having 1 to 8 C atoms, in the presence or absence of trialkylsilylchloride as catalyst and with a compound of formula IV $$KtA\qquad\qquad IV,$$

in which
Kt has the meaning of the organic cation $[Kt]^{z+}$ and
A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [BF$_4$]$^-$, [PF$_6$]$^-$, $[HSO_4]^{1-}$, [NO$_3$]$^-$, [(R$_2$)$_2$P(O)O]$^-$, [R$_2$P(O)O$_2$]$^{2-}$, [R$_1$O)$_2$P(O)O]$^-$, [R$_1$O)P(O)O$_2$]$^{2-}$, [(R$_1$O)R$_1$P(O)O]$^-$, tosylate, malonate which is optionally substituted by straight-chain or branched alkyl groups having 1 to 4 C atoms or [HOCO$_2$]$^-$, in which R$_1$ is each independently of another a straight-chain or branched alkyl group having 1 to 12 C atoms and R$_2$ is each independently of one another a straight-chain or branched perfluorinated alkyl group having 1 to 12 C atoms.

6. A process for preparing a compound of formula I according to claim 1, in which $[Kt]^{z+}$ is an organic cation, comprising reacting a compound of formula V $$[Kt]^{z+}[(R^1)BF_2(CN)]^-\qquad\qquad V$$

in which $[Kt]^{z+}$ and $R^1$ have a meaning as for the compound of formula I, with a compound of formula III $$(Alkyl)_3SiOR^*\qquad\qquad III,$$

in which Alkyl each independently denotes a straight-chain or branched alkyl having 1 to 8 C atoms and R* has a meaning as for the compound of formula I, or is trialkylsilylcyanide, in which the alkyl groups are each independently of one another straight-chain or branched alkyl having 1 to 8 C atoms.

7. A process for preparing a compound of formula I according to claim 1, in which $[Kt]^{z+}$ is another cation than the alkali metal cation in the starting material in a salt-exchange reaction, comprising reacting an alkali metal salt of formula I-1

$$[Me]^+[(R^1)B(CN)_2(OR^*)]^-\qquad\qquad I-1$$

in which $[Me]^+$ is an alkali metal cation and $R^1$ and R* have a meaning as for the compound of formula I, with a compound of formula IV $$KtA \qquad \qquad IV,$$

in which Kt has a meaning of an organic cation or an inorganic cation other than the alkali metal cation of the compound of formula I-1 and A denotes $F^-$, $Cl^-$, $Br^-$, $I^-$, $OH^-$, $[HF_2]^-$, $[CN]^-$, $[SCN]^-$, $[R_1COO]^-$, $[R_1OC(O)O]^-$, $[R_1SO_3]^-$, $[R_2COO]^-$, $[R_2SO_3]^-$, $[R_1OSO_3]^-$, $[SiF_6]^{2-}$, $[BF_4]^-$, $[PF_6]^-$, $[HSO_4]^{1-}$, $[NO_3]^-$, $[(R_2)_2P(O)O]^-$, $[R_2P(O)O_2]^{2-}$, $[R_1O)_2P(O)O]^-$, $[R_1O)P(O)O_2]^{2-}$, $[(R_1O)R_1P(O)O]^-$, tosylate, malonate which is optionally substituted by straight-chain or branched alkyl groups having 1 to 4 C atoms, $[HOCO_2]^-$ or $[CO_3]^{2-}$, in which $R_1$ is each independently of another a straight-chain or branched alkyl group having 1 to 12 C atoms and $R_2$ is each independently of one another a straight-chain or branched perfluorinated alkyl group having 1 to 12 C atoms.

8. An electrolyte formulation comprising at least one compound of formula I according to claim 1 and at least one further compound suitable for an electrolyte formulation.

9. An electrochemical and/or optoelectronic device comprising an electrolyte formulation according to claim 8 and at least one further component suitable for an electrochemical and/or optoelectronic device.

10. A product, which is a media for chemical reactions, a catalyst and/or a media in catalytical processes, a conducting salt, a component of electrolytes for the application in electrochemical cells, a component of supporting electrolytes for electrochemical processes, a surfactant, a phase-transfer catalyst, a trainer, an extractant, an antistatic additive, a plasticizer, a heat-transfer-medium, a modifier for membranes and textile materials, a lubricant, an additive to lubricant compositions or to engineering fluids, a hydraulic fluid, an additive to hydraulic fluids, a flame retardant or an additive to fire suppressing compositions, comprising a compound of formula I according to claim 1 in which $[Kt]^{z+}$ is an organic cation and z is 1, 2, 3 or 4 and at least one component or further compound suitable for an said product.

11. A product, which is a catalyst, a conducting salt, a component of electrolytes for the application in electrochemical cells, a component of supporting electrolytes for electrochemical processes, a surfactant, a phase-transfer catalyst or an antistatic additive, comprising a compound of formula I according to claim 1 in which $[Kt]^{z+}$ is an inorganic cation and at least one component or further compound suitable for an said product.

12. A conducting salt and/or component of electrolytes, comprising a compound of formula I according to claim 1 in which $[Kt]^{z+}$ is $Li^+$ and at least one component or further compound suitable for a conducting salt and/or component of electrolytes.

13. A method for the synthesis of a compound of formula I according to claim 1 in which $[Kt]^{z+}$ is an organic cation and z is 1, 2, 3 or 4 or an inorganic cation other than the alkali metal cation of the compound of formula I-1, comprising reacting a compound of formula I-1

$$[Me]^+[(R^1)B(CN)_2(OR^*)]^- \qquad (I-1)$$

in which Me is an alkali metal cation and $R^1$ and $R^*$ have a meaning as for the compound of formula I.

\* \* \* \* \*